(12) United States Patent
Rosen et al.

(10) Patent No.: US 10,025,906 B2
(45) Date of Patent: Jul. 17, 2018

(54) MOBILE SELF-MANAGEMENT COMPLIANCE AND NOTIFICATION METHOD, SYSTEM AND COMPUTER PROGRAM PRODUCT

(71) Applicant: LifeWIRE Corporation, Toronto, Ontario (CA)

(72) Inventors: Howard Rosen, Toronto (CA); William Harms, Driggs, ID (US); Chaitanya Marvici, Fort Collins, CO (US)

(73) Assignee: LifeWIRE Corporation, Toronto, Ontario (CA)

( * ) Notice: Subject to any disclaimer, the term of this patent is extended or adjusted under 35 U.S.C. 154(b) by 150 days.

(21) Appl. No.: 15/012,329

(22) Filed: Feb. 1, 2016

(65) Prior Publication Data
US 2016/0147970 A1    May 26, 2016

Related U.S. Application Data

(63) Continuation-in-part of application No. 14/849,421, filed on Sep. 9, 2015, now Pat. No. 9,715,578, which
(Continued)

(51) Int. Cl.
*A61B 5/00*        (2006.01)
*G06F 19/00*      (2018.01)
(Continued)

(52) U.S. Cl.
CPC ........ *G06F 19/3418* (2013.01); *A61B 5/0002* (2013.01); *G06F 17/3051* (2013.01);
(Continued)

(58) Field of Classification Search
None
See application file for complete search history.

(56) References Cited

U.S. PATENT DOCUMENTS

| 4,821,027 A | 4/1989 | Mallory et al. |
| 5,935,060 A | 8/1999 | Iliff |

(Continued)

OTHER PUBLICATIONS

Bell, KM & Orcutt, HK. (2009). Posttraumatic Stress Disorder and Male-Perpetrated Intimate Partner Violence. JAMA. 302(5):562-564.
(Continued)

*Primary Examiner* — John R Downey
*Assistant Examiner* — Shirley Jian
(74) *Attorney, Agent, or Firm* — Finnegan, Henderson, Farabow, Garrett & Dunner LLP

(57) ABSTRACT

A computerized interactive method, system and computer program product is provided for managing a person's health and lifestyle through self-managing controlled notifications, feedback, and alerts are disclosed. Embodiments provide computerized self-management and compliance scheme that does not require third party intervention or treatment options typical with immediate-response or alert-based systems. Monitoring, notification, and alert parameters can be partially or wholly self-managed using a graphical user interface or computerized device interface to enable two-way communication between the person and at least one computer server.

22 Claims, 16 Drawing Sheets

Related U.S. Application Data is a continuation of application No. 11/616,783, filed on Dec. 27, 2006, now Pat. No. 9,144,381.

(60) Provisional application No. 60/754,603, filed on Dec. 30, 2005.

(51) Int. Cl.
| | |
|---|---|
| *G06F 17/30* | (2006.01) |
| *G06Q 10/10* | (2012.01) |
| *G16H 50/20* | (2018.01) |
| *A61B 5/02* | (2006.01) |
| *A61B 5/145* | (2006.01) |
| *G16H 10/20* | (2018.01) |
| *G16H 10/60* | (2018.01) |
| *G16H 15/00* | (2018.01) |

(52) U.S. Cl.
CPC ... *G06F 17/30389* (2013.01); *G06Q 10/1097* (2013.01); *G16H 50/20* (2018.01); *A61B 5/02* (2013.01); *A61B 5/14532* (2013.01); *G16H 10/20* (2018.01); *G16H 10/60* (2018.01); *G16H 15/00* (2018.01)

(56) References Cited

U.S. PATENT DOCUMENTS

| | | | |
|---|---|---|---|
| 6,022,315 | A | 2/2000 | Iliff |
| 6,270,456 | B1 | 8/2001 | Iliff |
| 6,494,830 | B1 | 12/2002 | Wessel |
| 6,535,294 | B1 | 3/2003 | Arledge et al. |
| 6,641,532 | B2 | 11/2003 | Iliff |
| 6,656,114 | B1 | 12/2003 | Poulsen et al. |
| 6,728,341 | B1 | 4/2004 | Puchek et al. |
| 6,980,999 | B1 | 12/2005 | Grana |
| 7,090,638 | B2 | 8/2006 | Vidgen |
| 7,344,496 | B2 | 3/2008 | Iliff |
| 7,361,143 | B2 | 4/2008 | Kirchhoff et al. |
| 8,032,397 | B2 | 10/2011 | Lawless |
| 8,337,409 | B2 | 12/2012 | Iliff |
| 2003/0083556 | A1 | 5/2003 | Cosentino et al. |
| 2003/0229514 | A2 | 12/2003 | Brown |
| 2004/0030918 | A1 | 2/2004 | Karamchedu et al. |
| 2004/0054263 | A1 | 3/2004 | Moerman et al. |
| 2004/0059599 | A1 | 3/2004 | McIvor |
| 2004/0122702 | A1 | 6/2004 | Sabol et al. |
| 2005/0038326 | A1 | 2/2005 | Mathur |
| 2005/0113650 | A1 | 5/2005 | Pacione et al. |
| 2006/0031094 | A1* | 2/2006 | Cohen ............... A61M 5/1723 705/2 |
| 2006/0248183 | A1 | 11/2006 | Barton |
| 2007/0168228 | A1 | 7/2007 | Lawless |
| 2017/0004516 | A1* | 1/2017 | Hudson .............. G06Q 30/0203 |

OTHER PUBLICATIONS

Cohen, L.H., Guntherl, K.C., Butler, A.C., Parrish, B.P., Wenze, S.J. & Beck, J.S. (2008). Negative affective spillover daily events predicts early response to cognitive therapy for depression. Journal of Consulting and Clinical Psychology. 76(6), 955-965.
Collins, R., Kashdan, T. & Gollnisch, G. (2003). The feasibility of using cellular phones to collect ecological momentary assessment data: Application to alcohol consumption. Experimental and Clinical Psychopharmacology, 11(1), 73-78.
Freedman, M., Lester, K., McNamara, C., Milby, J. & Schumacher, J. (2006). Cell phones for ecological momentary assessment with cocaine-addicted homeless patients in treatment. Journal of Substance Abuse Treatment, 30(2), 105-111.
Gibbs, DA, Martin, SL, Kupper, LL, & Johnson RE. (2007). Child Maltreatment in Enlisted Soldier's Families during Combat-Related Deployments. Journal of the American Medical Association 298, No. (5): 528-535.
Gunthert, K.C., Cohen, L.H., Butler, A.C. & Beck, J.S. (2005). Predictive role of daily coping and affective reactivity in cognitive therapy outcome: application of daily process design to psychotherapy research. Behavior Therapy, 36, 77-88. Stone, A.A. & Shiffman, S. (1994). Ecological momentary assessment in behavioral medicine. Annals of Behavioral Medicine, 16, 199-202.
Hareva, D., Okada, H., Kitawaki, T., & Oka, H. (2009). Supportive intervention using a cell-phone in behavior modification. Acta Medica Okayama, 63(2), 113-120.
Krahn, D., Bohn, M., Henk, H., Grossman, J. & Gosnell, B. (2005). Patterns of Urges During Early Abstinence in Alcohol-dependent Subjects. American Journal on Addictions, 14(3), 248-255.
Moskowitz, D.S. & Young, S.N. (2005). Ecological momentary assessment: what it is and why it is a method of the future in clinical psychopharmacology. Journal of Psychiatry and Neuroscience. 31(1), 13-20.
National Council on Disability. (2009). Invisible Wounds: Serving Service Members and Veterans with PTSD and TBI. National Council on Disability, Washington DC. Mar. 4, 2009.
RAND Corporation. 2009. Assessing Combat Exposure and PTSD in Troops and Estimating the Costs to Society: Implications from the RAND Invisible Wounds of War Study. RAND Corporation, Alexandria, VA. Mar. 2009.
Reid, S.C., Kauer, S.D., Dudgeon, P., Sancl, L.A., Shrier, L.A. & Patton, G.C. (2005). A cell-phone program to track young people's experiences of mood, stress and coping. Social Psychiatry Epidemiology, 44, 501-507.
Trull, T. & Ebner-Priemer, U. (2009). Using experience sampling methods/ecological momentary assessment (ESM/EMA) in clinical assessment and clinical research: Introduction to the special section Psychological Assessment, 21(4), 457-462.
Waters, A. & Li, Y. (2008). Evaluating the utility of administering a reaction time task in an ecological momentary assessment study. Psychopharmacology, 197(1), 25-35.
American Association of Clinical Endocrinologists (AACE ), (2003-2004). The State of Diabetes in America; A Comprehensive Report.
The New England Journal of Medicine (NEJM), (2005). Intensive Diabetes Treatment and Cardiovascular Disease in Patients with Type I Diabetes. Abstract.
Non-final Office Action issued in U.S. Appl. No. 11/616,783 dated Jun. 25, 2008.
Final Office Action issued in U.S. Appl. No. 11/616,783 dated Dec. 29, 2008.
Non-final Office Action issued in U.S. Appl. No. 11/616,783 dated Jun. 5, 2009.
Final Office Action issued in U.S. Appl. No. 11/616,783 dated Mar. 31, 2010.
Final Office Action issued in U.S. Appl. No. 11/616,783 dated Oct. 11, 2012.
Non-final Office Action issued in U.S. Appl. No. 11/616,783 dated Sep. 30, 2014.
Final Office Action issued in U.S. Appl. No. 11/616,783 dated May 5, 2015.

* cited by examiner

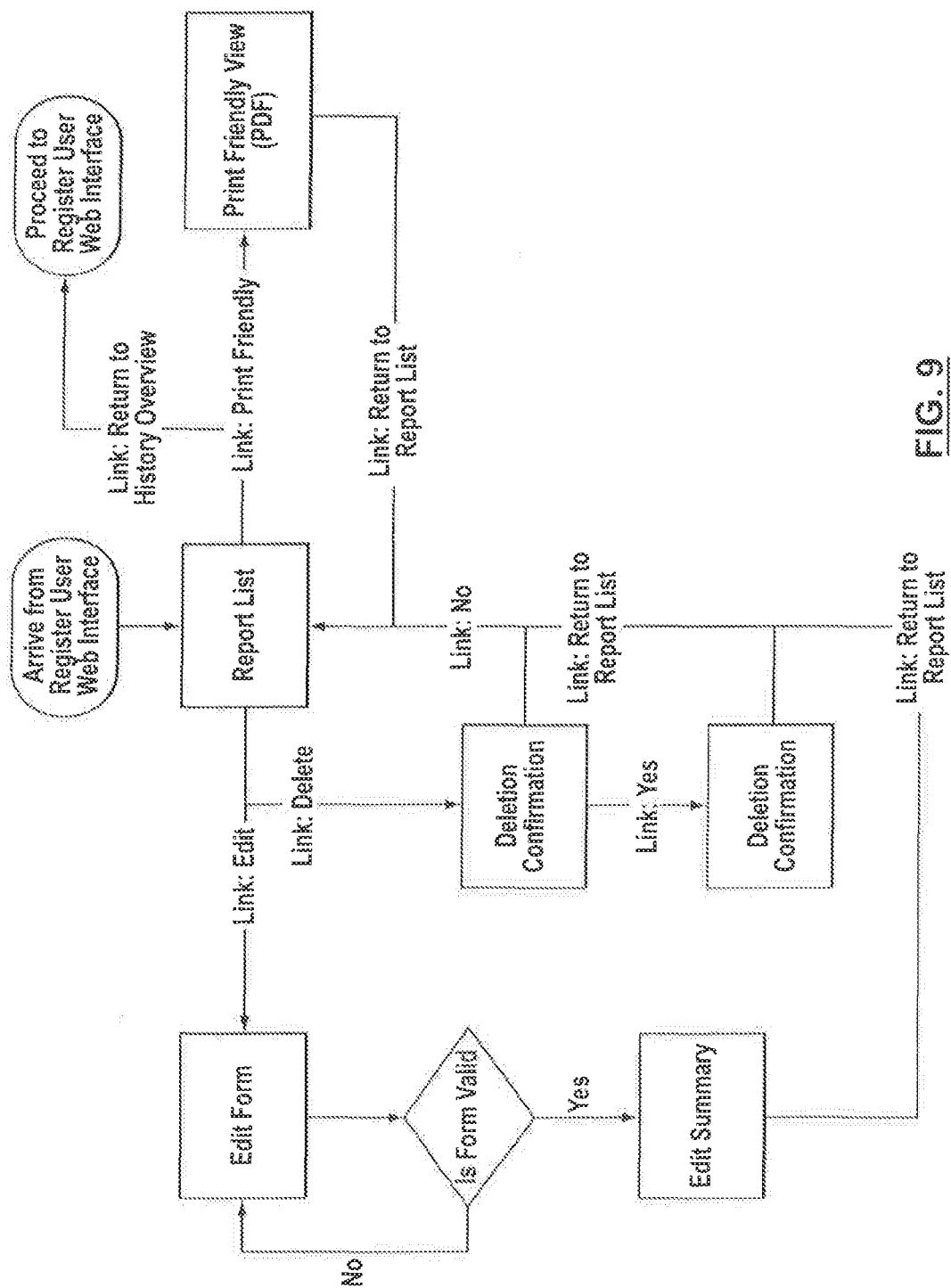

FIG. 15

MOBILE SELF-MANAGEMENT COMPLIANCE AND NOTIFICATION METHOD, SYSTEM AND COMPUTER PROGRAM PRODUCT

I. CROSS REFERENCE TO RELATED APPLICATIONS

This application is a continuation-in-part of application Ser. No. 14/849,421, filed Sep. 9, 2015, which is a continuation of U.S. application Ser. No. 11/616,783, filed on Dec. 27, 2006, now U.S. Pat. No. 9,144,381, which claims the benefit of U.S. Provisional Application No. 60/754,603, filed on Dec. 30, 2005, all of which are incorporated herein by reference in their entirety.

II. TECHNICAL FIELD

This disclosure generally relates to communication systems for improving user compliance and computerized health monitoring. More particularly, this disclosure relates to computerized interactive communication systems for monitoring health.

III. BACKGROUND

For patients suffering from chronic illness, monitoring of their condition and ensuring compliance of health regimes are vital to their long term health. However, patients are often unsuccessful at keeping proper records of health statistics related to their condition. Logbooks, PDAs and computers adapted to monitor their conditions often become a burden, furthering their suffering instead of being a tool to assist them in effectively dealing with their condition.

In general, the ability to ensure the monitoring and response to changing physiological conditions in real time gives the patient the ability to react to their condition before an emergency occurs. The improved care through direct patient management means reduced costs associated with chronic conditions: less physician visits, less hospital visits and fewer sick days.

Diabetes is an example of a particularly difficult chronic condition requiring constant monitoring and attention by the patient. Diabetes is associated with an increased risk for a number of serious, often life-threatening complications and certain groups may experience an even greater threat. There are currently approximately 20 million people in North America alone suffering from diabetes; this number is estimated to climb to 45 million by 2010. Good diabetes management can help reduce risk. However, approximately 70% of diabetics do not manage their disease. In recent report issued by the American Association of Clinical Endocrinologists (AACE) entitled the "State of Diabetes in America", blood sugar control across the United States was examined. The findings revealed that approximately two out of three Americans with type 2 diabetes analyzed in the study did not reach the AACE-recommended target blood sugar goal in 2003 and 2004.

Further, studies in the United States and abroad have found that improved glycemic control benefits people with either type 1 or type 2 diabetes. In fact, after a 17 year federal study, the New England Journal of Medicine reported in the Dec. 22, 2005 issue that "intense control of blood sugar prevents heart attacks and strokes by nearly 50%." According to the American Diabetes Association, every percentage point drop in A1C blood test results (e.g., from 8.0% to 7.0%) reduces the risk of microvascular complications (e.g., eye, kidney, and nerve diseases) by 40%.

Cardiovascular disease, such as heart disease or stroke, is another example of a particularly difficult chronic condition that can benefit from constant monitoring and attention by the patient. For example, controlling blood pressure reduces the risk of cardiovascular disease among persons with diabetes by 33% to 50% and the risk of microvascular complications by approximately 33% according to American Diabetes Associates. In general, for every 10 mm Hg reduction in systolic blood pressure, the risk for any complication related to diabetes is reduced by 12%. The control of blood lipids also is important, with studies showing that improved control of cholesterol or blood lipids (for example, HDL, LDL, and triglycerides) can reduce cardiovascular complications by 20% to 50%.

In addition to those suffering from chronic disease, preventative medicine often requires the monitoring of specific health-related statistics. For example, the monitoring of blood pressure and cholesterol is necessary for many people, especially those with a family history of cardiac problems. Moreover, so-called "pre-diabetics" are advised to keep close watch on their glucose level as a preventative measure in avoiding the full blown disease.

IV. SUMMARY

The present disclosure discloses a remote interactive method, system and computer program product for self-managing a person's regular lifestyle needs and attributes through a controlled notification and feedback system that monitors and ensures compliance.

In one embodiment, the system includes an input device comprising a communication means, a set-up means, a set-up notification means, an approval means, and a notification and data analysis means. The system furthermore comprises a user and administrator back-end means which includes a compliance measurement means.

The system provides for feedback and measurement for healthcare provides to ensure that those under their care are complying with notifications and respective regimes.

In that regard, the disclosed system involves three compliance related elements: (i) relating to the direct management with a user; (ii) monitoring such compliance; and (iii) on the business model, creating an incentive for the user to use the disclosed system over and above health concerns.

The system and method provides a simple, cost effective, and flexible self-management that does not require a third party intervention or treatment options on an immediate response or alert based system. The system provides for a long term management, compliance and analysis for the benefit of the individual. In implementing this method in a healthcare environment, the individual will gain a better understanding of managing their lifestyle and behavior and allow for healthcare managers to measure compliance of certain activities (if required). Further, employing already existing and available low cost technology improves the rate of patient data capture.

Users are responsible for tailoring the setup to their particular needs. Queries, notifications, reminders, and/or alerts are provided on a regularly basis, prompting users to take necessary quantitative or qualitative measurements, medication, or to record particular activities or conditions. These notifications can be tailored in a number of ways. For example, the users can choose to monitor the particular attribute or attributes that are relevant to their condition, including glucose level, temperature, blood pressure, heart rate, weight, medication intake, pain characteristics, etc. The user is able to choose the number of notifications, and schedule them appropriately. The system confirms the input from the user, resulting in a reduction in the possibility of error. Such input in monitored, allowing the ability to ensure compliance or to determine the extent of compliance of the user.

The disclosed system utilizes SMS ("Short Message Service") and MMS ("Multimedia Message Service") technology with ordinary cellular phones or other personal communication devices. The disclosed system is advantageous in this respect, since it relies on existing SMS/MMS telecommunication technology and technology owned by the user, and not specialized hardware. However, the phone is not the only means of data entry; information can be entered into the system via an Internet portal. Furthermore, a skilled artisan would recognize that the disclosed system may utilize alternative technology to SMS or MMS technology. For example, email, social-media messages/notifications, smartphone App notifications, or smartwatch notifications may be used in place of SMS or MMS technology.

The system comprises two separate interfaces in this respect: (i) a consumer interface; and (ii) a system administrator interface. The user is prompted for information, e.g., notification attributes, and the information is submitted back to the server. Based on disease-specific protocols determined by the user, the data can be analyzed immediately to identity trends, especially the detection of worsening conditions. Based on user-configured rules, family and other care-givers can be notified immediately of any adverse trends.

Users and their healthcare network can access more detailed information regarding the data collected through a web interface. The raw input data, basic trends and charts show the patients' most recent information as well as historical information which can all be printed out. Analytical tools can also be created and linked with the database. In addition, the healthcare provider and/or caregiver can also, based on the information, 'push' key messages via the disclosed system to a user or group of users depending on the circumstances.

The disclosed system also contemplates the pairing of other hardware, apart from personal communication devices, with the notification and feedback means. For example, patients can link "smart" BLUETOOTH™ enabled glucometers directly with the system or similar 'smart' monitors relating to measurements such as blood pressure, heart rate or even distance run. Furthermore, a global positioning device could be linked with the system or within the communication device to provide an advantageous feature if patient location monitoring is desired or analytics as to past or future location related behavior. Hardware can also be adapted within the communication device such as biometric sensors to allow for quantitative measurements of the various attributes.

The disclosed system is preferably employed to provide monitoring and compliance systems for patients suffering from Diabetes, with the input data being related to glucose levels and/or blood pressure information. The disclosed system contemplates the monitoring of a plurality of measurements as opposed to just a single measurement. For example, Diabetes-related monitoring can consist of glucose levels, blood pressure values, heart rate, temperature, etc., or compliance issues such as whether medication has been taken and whether a user has exercised as may be required. It is to be expressly understood that monitoring of Diabetes-related conditions is only an example of an implementation, and the disclosed system contemplates various other applications, as discussed herein.

In an aspect of the disclosed embodiments, the monitoring system is employed to monitor the blood pressure data of a user. In a further aspect of the disclosed embodiment, the monitoring system can be used to track multiple measurements for patients who have undergone organ transplant. The disclosed system can also be employed to monitor a patient's thyroid condition, or to track Alzheimer's sufferers, or used to determine the mobility status of Arthritis sufferers, or as a means to record and monitor the medication intake and compliance for anyone on a specific medication regiment. The disclosed system is also well-suited for both diet management and related analysis, and exercise management and related analysis.

Further, the disclosed system is also operable to prompt the user for specific non-quantitative health or lifestyle related information related to any of the applications discussed herein.

In further aspects of the disclosed embodiments, the monitoring system can be utilized for specific non-health related purposes, including but not limited to the following: maintaining contact with children; maintaining conduct with adults requiring supervision, such as with prison inmates, people involved in extreme-style sports such as skiing or cross country running, walkers, joggers, bike riders, etc.; meeting notification; reminder notification; travel or location updates (i.e. for people keeping track of travelers, such as children); fleet attributes such as gas consumption (input of fuel used and distance traveled); any type of location/trend analysis, including trend analysis involving a combination of location/activity and other data (e.g., tracking activity with glucose level or blood pressure); general remote input of an activity on a regular basis and analyzed for access by user and approved user(s); and/or general notification reminder system based on pre-determined parameters.

In yet a further aspect of the disclosed embodiments, the disclosed system is adaptable to a business model whereby revenue is generated from the collection of service fees.

V. BRIEF DESCRIPTION OF THE DRAWINGS

A detailed description of the preferred embodiments is provided herein below by way of example only and with reference to the following drawings, in which:

FIG. 9 is a flowchart illustrating a further aspect of one particular embodiment of the present disclosure, namely a blood sugar report management system.

FIG. 15 is an illustration of an example of a clinical interface, consistent with embodiments of the present disclosure.

Figure 1A:
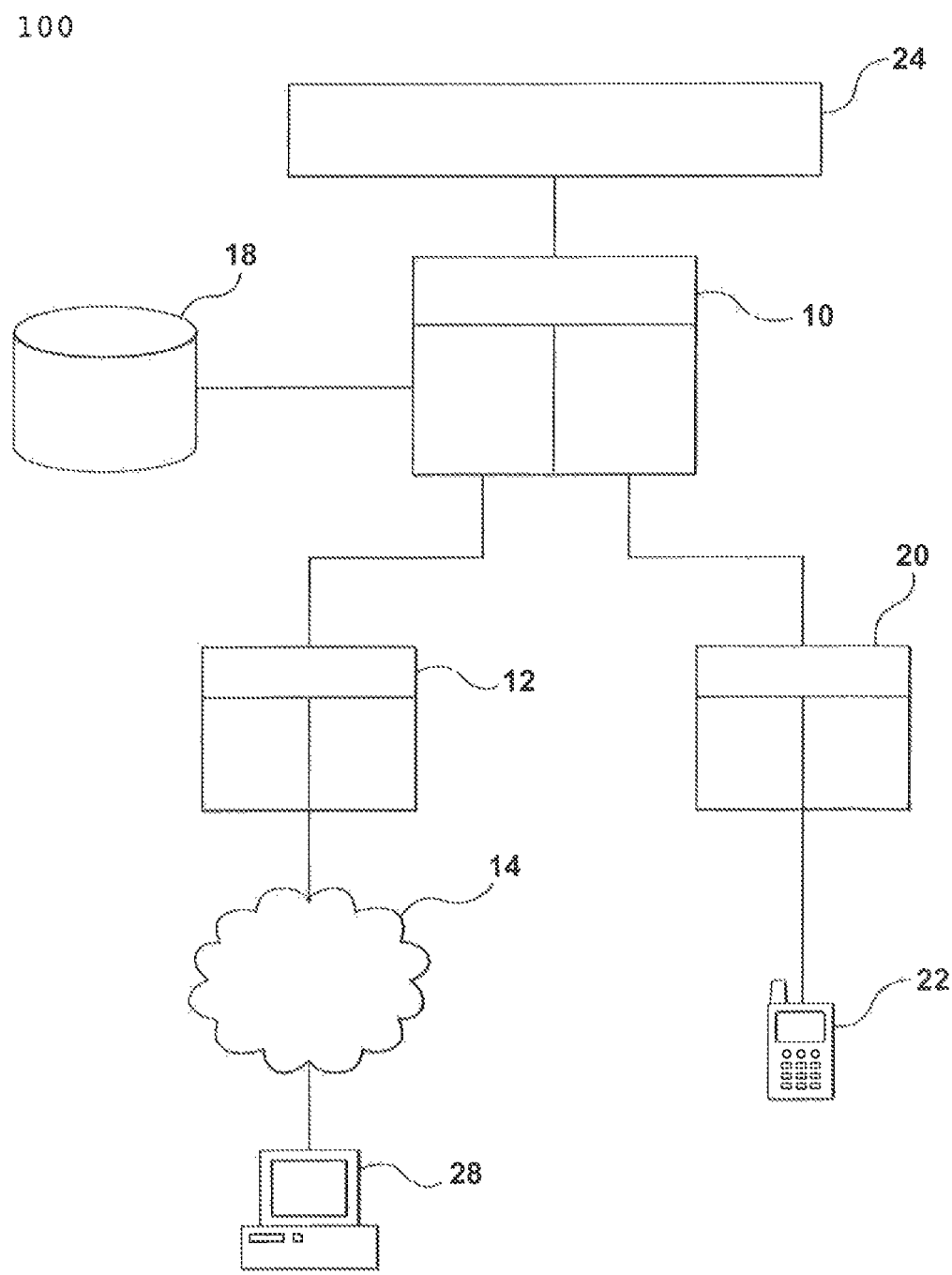
FIG. 1A is a system diagram of a system, consistent with disclosed embodiments.

In the drawings, one embodiment of the disclosure is illustrated by way of example. It is to be expressly understood that the description and drawings are only for the purpose of illustration and as an aid to understanding, and are not intended as a definition of the limits of the disclosure.

VI. DETAILED DESCRIPTION

As discussed above, monitoring of patients' condition and ensuring their compliance to health regimes are vital to their long term health. Disclosed herein is, among other things, an interactive lifestyle monitoring system that may improve monitoring of patients' condition and improve compliance of health regimes. For example, the disclosed system may improve monitoring patients' conditions, such as glucose levels, blood pressure, discomfort level, and how the patient is feeling. Additionally, the system may improve patients' compliance (i.e., adherence) of health regimes by, for example, improving patients' medication adherence and improving compliance of their exercise regimes.

The disclosed system may use mobile devices and may facilitate self-management of conditions by the patients.

The disclosed system contemplates the use of personal communication devices that provide technological means to measure and health or lifestyle related information of the user and subsequently communicate the information. As an example, "smart glucometers" can be employed by the user to reply to notifications by communicating glucose levels in accordance with an embodiment of the present invention. Other advanced personal communication devices can be employed having the capabilities to take a user's temperature, measure blood pressure, heart rate, etc. Furthermore, sensors can be embedded into the personal communication device such as a cell phone that can quantitatively measure attributes such as temperature, heart rate, etc.

The user selects the interval time period to which the trend analysis is conducted by the system. As a default, trend analysis is conducted for every ten measurements, for example. The user also determines and selects the parameters for the trends in terms of when to issue notifications. The user specifies who, if anyone, should be sent an alert or notification when said notification parameters are met.

FIG. 1A illustrates an exemplary system 100, consistent with disclosed embodiments. As shown in FIG. 1A, system 100 may include a server 10, and server 10 may include a web server 12, a telephony server 20, a server application 24, and/or database 18. In some embodiments, server 10 may be connected to one or more devices or computers that implement the function of web server 12, a telephony server 20, a server application 24, and/or database 18. Database 18 receive and store data associated with one or more processes disclosed herein, under the control of server 10 and/or one or more other processors in communication with database 18. In some embodiments, database 18 may store one or more programs or other computer-executable code that, when executed, cause one or more processors to perform functions and methods associated with disclosed embodiments.

Still referring to FIG. 1A, system 100 may further include client devices such as a personal computer 28 and/or a cellular phone 22. In some embodiments, personal computer 28 may be connected to web server 12 through the Internet 14, and cellular phone 22 may be connected to telephony server 20. System 100 illustrates both the personal computer 28 and a cellular phone 22, however, some systems may include only one type of client devices.

Still referring to FIG. 1A, server 10 includes server application 24. In some embodiments, server application 24 may include one or more software (e.g., a script or a program) that enables the processing steps described below and supports the described functions.

Figure 1B:
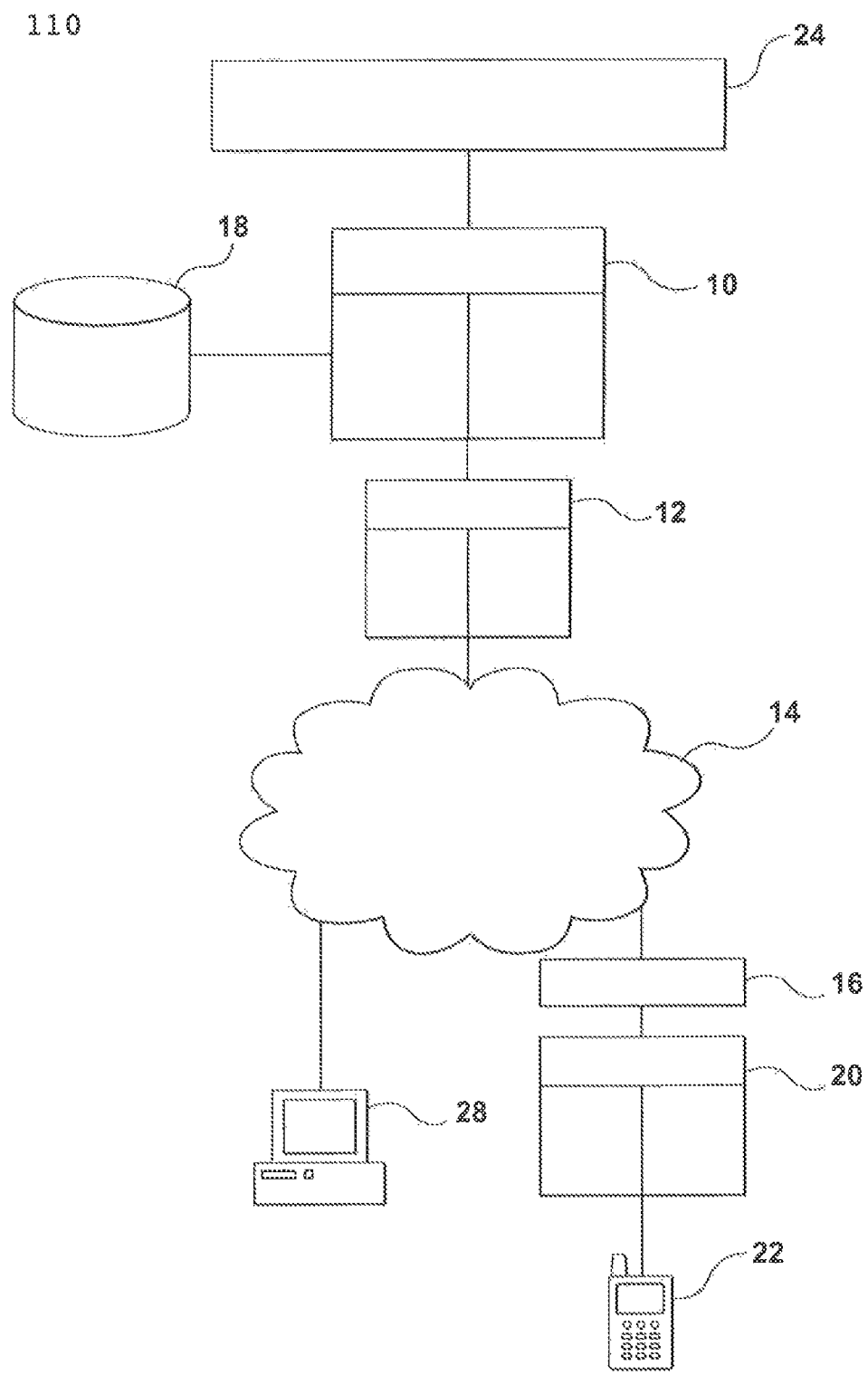
FIG. 1B is a system diagram of another system, consistent with disclosed embodiments.

FIG. 1B illustrates another exemplary system 110, consistent with disclosed embodiments. System 110 is similar to system 100 of FIG. 1A except that telephony server 20 supports the connection between communication device 20 and server 10 via the Internet 14 through a wireless gateway 16. For purposes of discussion, the system performing disclosed methods and processes is referred to as "system 100," however in some embodiments system 110 can perform the disclosed methods and processes.

Figure 2A:
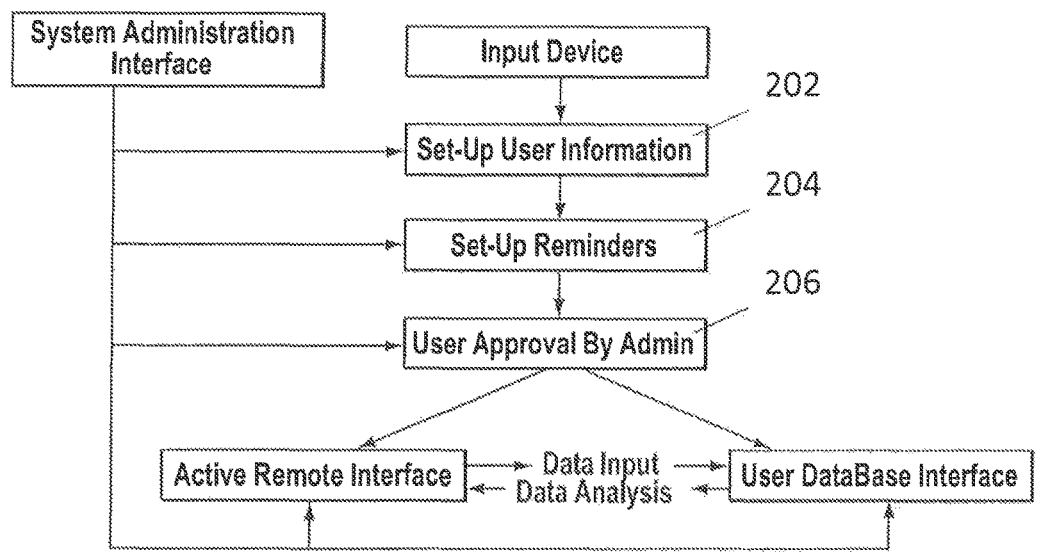
FIG. 2A is a flow diagram of an exemplary process performed by a system, consistent with disclosed embodiments.

FIG. 2A is a flow diagram of an exemplary process 200, consistent with disclosed embodiments. Process 200 may be performed by a system such as system 100 or system 110.

At step 202, the user may set-up a user account using an input component of a device. The device may include, for example, a personal computer or a cellphone, and the input component may include, for example, number pads, keyboard, or a voice-recognition system. In systems that use a voice-recognition system, the information entered by the user may be verified for accuracy in an additional step. In one example, a user may setup an account using one or more personal computers 28 configured to communicate with the web server 12 via the Internet 14. For example, the user may use personal computer 28 to access a system website hosted on web server 12, and enter a set of information requested by the system website using input devices of personal computer 28. The set of information requested may include user information and other information that may be needed to set up a user account. In some embodiments, the information may include information to password protect the user account. In some embodiments, the user may be a patient, however, in other embodiments, the user may be a person acting on behalf of the patient.

In some embodiments, at least one custom-defined attribute ("user tag") may be created and associated with the user account. In some embodiments, each user tag may include a key and a value. The key of the user tag may include a description of a data, and the value of the user tag may include the data itself. The user tag may be associated with an item to be included in a query to or from the user. For example, a key of the user tag may be the text "birthday" and the value of the user tag may be the birthday of the user. In another example, a key of the user tag may be the text "delivery date," and a value of the user tag may be the delivery date of the pregnant user. In yet another example, a key of the user tag may be the text "nickname" and the value of the user tag may be the preferred nick name of the patient. In a further example, a key of the user tag may be the text "doctor" and the value of the user tag may be a name or identification of a physician associated with the user. In some embodiments, one or more user tags may be created and associated with a user account by the user. In these embodiments, the user may enter the key and the value of the user tags using while creating the user tag. In other embodiments, the user may select a predetermined key, and enter a value of the user tag.

Alternatively, or additionally, one or more user tags may be created and associated with one or more user accounts by an administrator. In some examples, the administrator may enter both the key and the value (i.e., default value) for each of the user tags created by the administrator, and the user may change the values of one or more user tags created by the administrator at a later time. Alternatively, the administrator may enter only the key for each of the user tags created by the administrator, and the user may be required to enter the initial values of the user tags created by the administrator during the user account set-up process. In some embodiments, the administrator may be one of healthcare professionals caring for the patient. In some embodiments, the administrator may load a set of user tags that was pre-created and associate the loaded user tags with one or more user accounts.

In some embodiments, a value of a user tag may be generated automatically by the system. For example, a key of a user tag may be the text "Capitals Fan" and a value of the user tag may be the latest hockey game score involving the Capitals team retrieved by server 10 of the system from the Internet. In some embodiments, a value of a user tag may be generated by the system based on another user tag. For example, a key of a user tag may be the text "Home Weather" and a value of the user tag may be the weather information retrieved by the system based on a value of another user tag with a key "Home Address."

At step 204, the user may configure settings for notification and monitoring parameters. In some embodiments, the user may configure settings for notification and monitoring parameters by selecting from a set of settings for notification and monitoring parameters configured by the administrator. In some embodiments, the settings for notification and monitoring parameters may include a query setting and an alert setting. The query setting may include, for example, a query schedule and the alert setting may include at least an alert criterion and an alert procedure that corresponds to each alert criterion. In some embodiments, the query setting may further include a query type. The query type may be, for example, one of: single query, multiple queries with no immediate response required, and multiple queries with a response dependent on input.

The query schedule may determine when one or more queries are sent to the user's device. In some embodiments, the query schedule may include the number of queries the user receives in one day. In some examples, the user may elect to receive one to six queries per day. In other examples, the user may elect to receive more than six queries per day. In yet another example, the user may select not to receive any query. Additionally, the query schedule may include a specific time and/or date at which one or more queries should be sent to the user's device.

The alert criterion may define a condition in which the alert procedure is executed. In some embodiments, the alert criterion may be defined in terms of the response data provided by the user for a particular query. For example, the alert criterion may be defined such that the alert procedure is executed when a response data to a query is above or below a predetermined value. In another example, the alert criterion may be defined such that the alert procedure is executed when a response data for a query is above or below the cumulative average of the response data.

In some embodiments, the alert procedure may define a set of actions executed by the system when the alert criterion is met. The set of actions may include contacting one or more people based on information user entered while configuring settings for notification and monitoring parameters or based on one or more user tags. For example, when an alert procedure is executed, system 100 may retrieve a list of people identified in the settings for notification and monitoring parameters and contact everyone in the list using an SMS message. The SMS message may include a message indicating that the user is in need of assistance, for example. In another example, when an alert procedure is executed, system 100 may retrieve the value associated with the user tag with the key "Best Friend" and contact the user's best friend using the value of the user tag. The user tag value may be, for example, an email or a phone number, and system may determine the appropriate method of contacting the user's best friend depending on the type of contact information contained in the user tag.

In some embodiments, the set of actions defined by an alert procedure may include notifying a device associated with the administrator. The notification may include the details of the response data and the query that caused the alert procedure to be executed. In some embodiments, the notification to the administrator may include options for the administrator to select. These options may include, for example, an option to contact one or more people (e.g., people the user has preauthorized or other healthcare professionals). In another example, these options may include an option to generate/load and send additional queries to the user.

In some embodiments, the user may determine whether they want SMS notification to be sent to their mobile devices, such as their cellular phones (not shown in figures).

At step 206, the account may be approved by an administrator. Subsequently, queries are sent to the user based on the query setting, and the user provides response data corresponding to each query to the system. Alternatively, a query may be, for example, an alert or a reminder that requires no response data from the user. In the next step, user's response data are analyzed.

After the account is approved by an administrator, in some embodiments, at least one query may be sent to the user when an input data is received at server 10 from the user's device. In these embodiments, the input data may include a text data or a keyword that corresponds to one or more predetermined queries, and upon receiving the input data, server 10 may send the corresponding predetermined one or more queries to the user's device.

In some embodiments, server 10 of the system may generate and send at least one additional query to the user's device based on the analysis of the response data. Alternatively, server 10 of the system may load and send a set of preconfigured queries. Consider an example where the queries are directed to determining the user's level of depression. If the analysis of the response data from these queries indicate that the user may be depressed, a set of queries that has been validated and/or approved by FDA or similar authority for health interactions to diagnose depression may be loaded and sent to the user's device. In some embodiments, these additional queries may be automatically loaded and sent by the system 100 based on the analysis of the response data. In other embodiments, the administrator's input may be solicited, as discussed above. For example, a notification may be sent to the administrator based on the response data, and the notification may include options to generate/load and send additional queries to the user. In some examples, the administrator may load the additional queries to send from a library of query sets included in the system 100. In these examples, each query set may be preconfigured based on a study and/or may be a validated set of queries for a certain condition.

In some embodiments, a clinical interface may be displayed to a device associated with the administrator during process 200. A "clinical interface" may be a graphical interface for providing filtered, concise data to an administrator in an intuitive and easy to comprehend format to facilitate the use of those compiled data in treatment planning and execution. Specifically, the administrator may determine the parameters, rules, and variables to measure for one patient, some patients or the entire population, and the clinical interface may provide a "snap shot" of how an individual patient is faring compared to the population as a whole. Thus, the administrator may use the clinical interface to determine how that patient would do in the future, under the same parameters.

In some embodiments, the clinical interface may display data to aid an administrator in determining a treatment. The clinical interface may also display summarized data with an option for the administrator to access complete data. In some embodiments, the clinical interface may be updated in real-time (e.g., the clinical interface may be updated when an additional response data from a user is received).

The clinical interface may display data that is charted in both raw and calculated formats. When data is analyzed for changes over a period of time, for example, each response data may be compared to the running mean of that response data. This process may serve to make all observations relative to the individual rather than an external standard or value.

In some embodiments, the clinical interface may include a table view. In one example, the table view may display a value representing a change in the response data over a period of time. In another example, the table view may display a value representing a cumulative mean of the response data. In yet another example, the table view may display a value calculated based on the response data received from multiple patients in the same treatment group. In this example, the clinical interface may aid the administrator in evaluating how each patient's response data compares to that of their treatment group. The same treatment group may be defined as, for example, a group of patients participating in the same treatment sequence and/or at the same facility.

Figure 15:
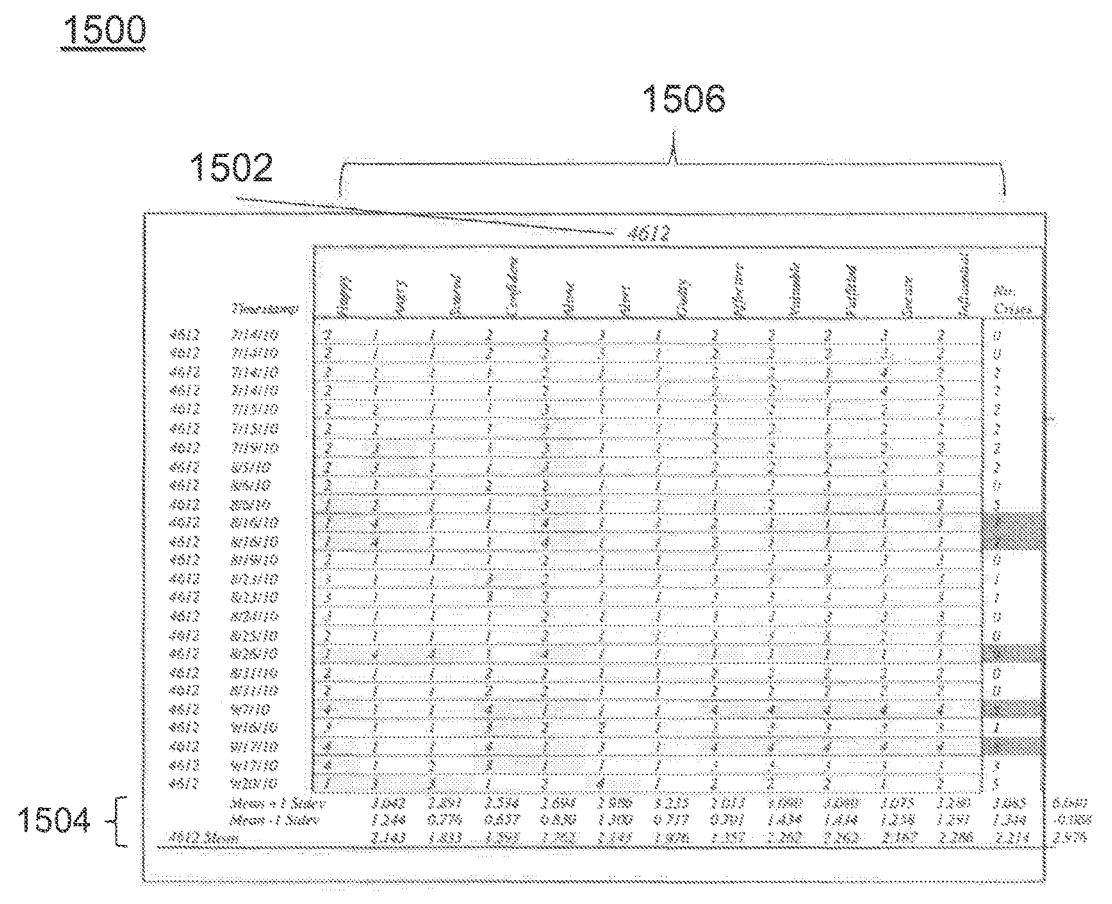

FIG. 15 shows an example of clinical interface 1500, consistent with disclosed embodiments. Clinical interface 1500 includes a table view 1506 displaying response data by a patient and a label 1502 identifying the patient. In some embodiments, clinical interface 1500 may also include statistical data 1504 which includes cumulative mean and mean+/−standard deviation for each column in the table view.

Figure 2B:
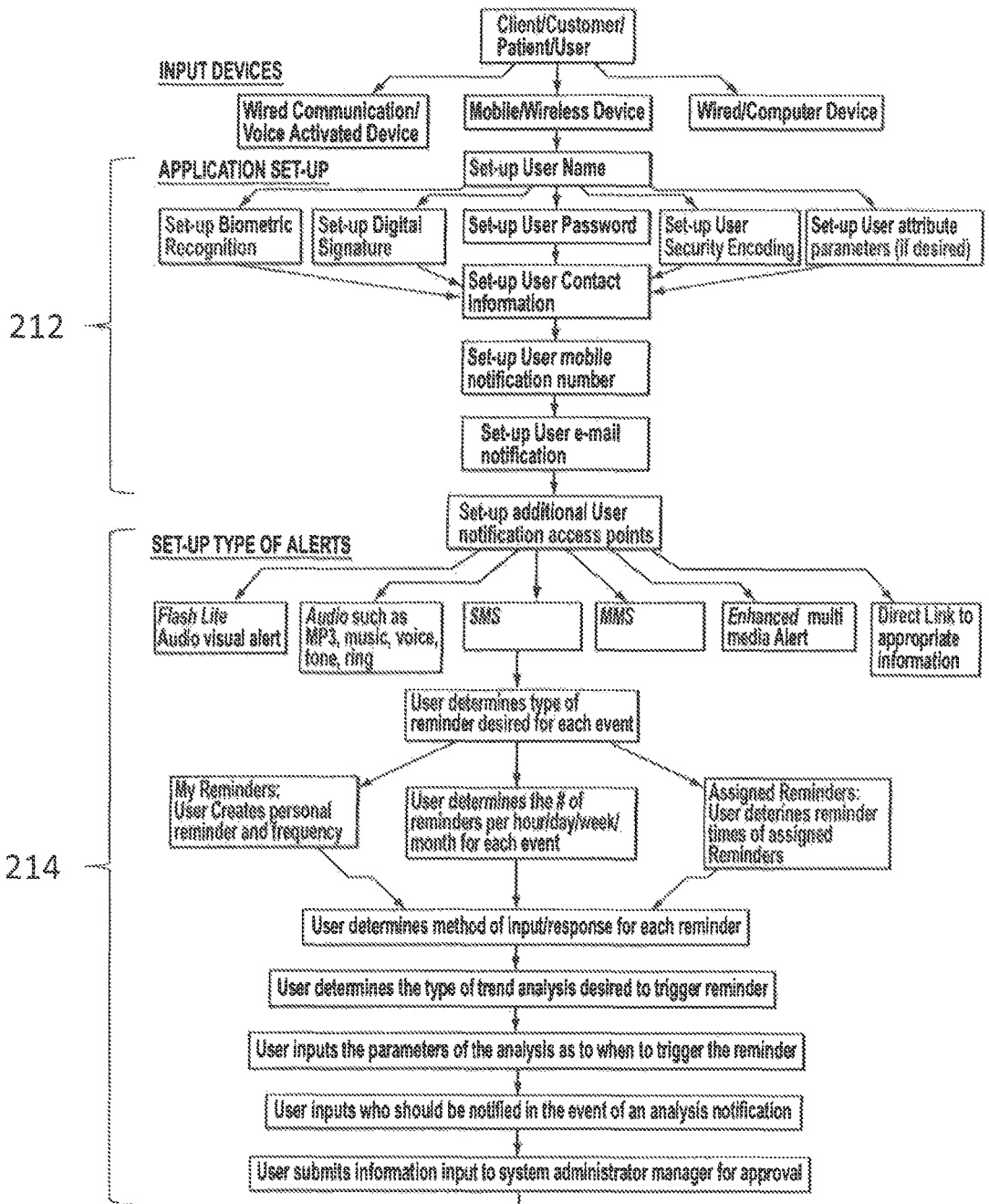
FIG. 2B is a flow diagram of an exemplary process for setting up user information, consistent with disclosed embodiments.

FIG. 2B is a flow diagram of an exemplary process 210 for setting up user information, consistent with disclosed embodiments. In some examples, process 210 may be performed at step 204 of FIG. 2A. At step 212, the user may use one or more input devices to provide information requested by a system 100. In some embodiments, the requested information may include information to protect the user account. For example, the requested information may include user's biometric data, digital signature, user ID and password, user security encoding information, or a combination thereof. In some embodiments, the requested information may include attribute parameters, which are elements that would allow the system to better assign questions/notifications worded in a manner most likely preferred by the user. Attribute parameters may also enable the system to group the users with similar attributes for chats, support, etc. The user thus establishes the notification scheme based on their own interactive lifestyle monitoring needs. In some embodiments, the requested information may include user's contact information, information for setting up mobile notification, and/or user's email address.

At step 214, the user may configure settings for notification and monitoring parameters. The queries can be set-up in a plurality of ways, for example, single query, multiple query with no immediate response required, or multiple query with a response dependent on input. The user may determine the nature of the one or more elements measured or may be pre-determined by a third party administrator for the user. Alternatively, the administrator may provide a range of pre-configured queries from which the user may select from. In addition, a user may desire notifications for multiple events (e.g., glucose, blood pressure, etc.). A user may also specify that the wish to response via alternate means than used to remind (e.g., SMS notification but a response via computer). The parameters for analysis for triggering the notification (i.e. a reminder or an alert) can be established either by the user or by a third party administrator.

Figure 2C:
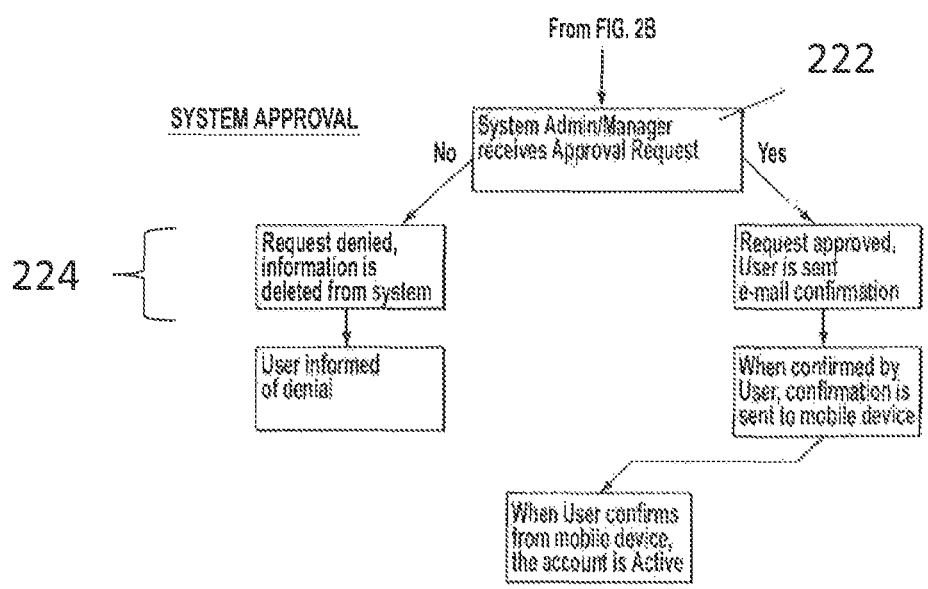
FIG. 2C is a flow diagram of an approval process, consistent with disclosed embodiments.

FIG. 2C is a flow diagram of an approval process 220, consistent with disclosed embodiments. Process 220 begins after the user submits all relevant and required information to a system administrator or manager ("administrator") for approval. The submitted information may include the settings for notification and monitoring parameters. In some examples, process 220 may be performed at step 206 of FIG. 2A.

At step 222, the administrator receives the approval request that includes settings for notification and monitoring parameters.

At step 224, the administrator may approve or deny the request. In some embodiments, the administrator may modify the settings for notification and monitoring parameters prior to step 224. For example, the administrator may alter, add, or remove a query schedule, alert criterion, and alert procedure. In some embodiments, the administrator may also generate additional queries associated with the user account based on one or more user tags. In an example where a user tag has the text "delivery date" as the key and the user tag is associated with the user's account, the administrator may instruct the system 100 to generate additional query schedules for significant post-partum dates (e.g., 1 week, 1 month, and/or 3 months after the delivery date) based on the value of the user tag (i.e. date of delivery). In some embodiments, these additional query schedules may be manually created by the administrator. In some embodiments, the device used by the administrator may aid the generation of additional notifications. For example, the device used by the administrator may display one or more suggested queries schedules based on one or more user tags. Therefore, instead of creating the additional queries by manually entering required information, the administrator may create the additional queries by simply selecting one or more of the suggested notifications. The suggested notifications may be generated using one or more algorithms pre-programmed in the system 100, and these algorithms may be derived from one or more clinical studies or in consultation with a medical professional. Additionally, these suggested notifications may be generated at server 10 of the system 100, or alternatively, at a device such as personal computer 28 or cellular phone 22 used by the administrator.

After the approval process, approval information may be sent from the device used by the administrator to server 10 of system 100. The approval information may include information relating to whether monitoring scheme proposed by the user is approved, and may optionally include modified settings for notification and monitoring parameters.

Server 10 of system 100, upon receiving the approval information, may activate the proposed monitoring scheme (or the modified monitoring scheme, if included in the approval information).

Additionally, upon activation of a monitoring scheme, server 10 of system 100 may generate queries based on the query setting of the activated monitoring scheme and send the generated queries to the user's device based on the query schedule of the activated monitoring scheme.

In embodiments where one or more user tags are created and associated with the user account, notifications and queries may be generated based on one or more user tag values. In an example where a key of a user tag is the text "nick name," the query may use the value of the user tag, which is the preferred nickname of the user, instead of the full name of the user. In another example, a key of a user tag may be the text "Capitals Fan" and the value of the user tag may be the latest, dynamically retrieved score of a hockey game involving the hockey team, Capitals. In this example, a notification may include the score of the hockey game at the time it is generated.

Figure 3:
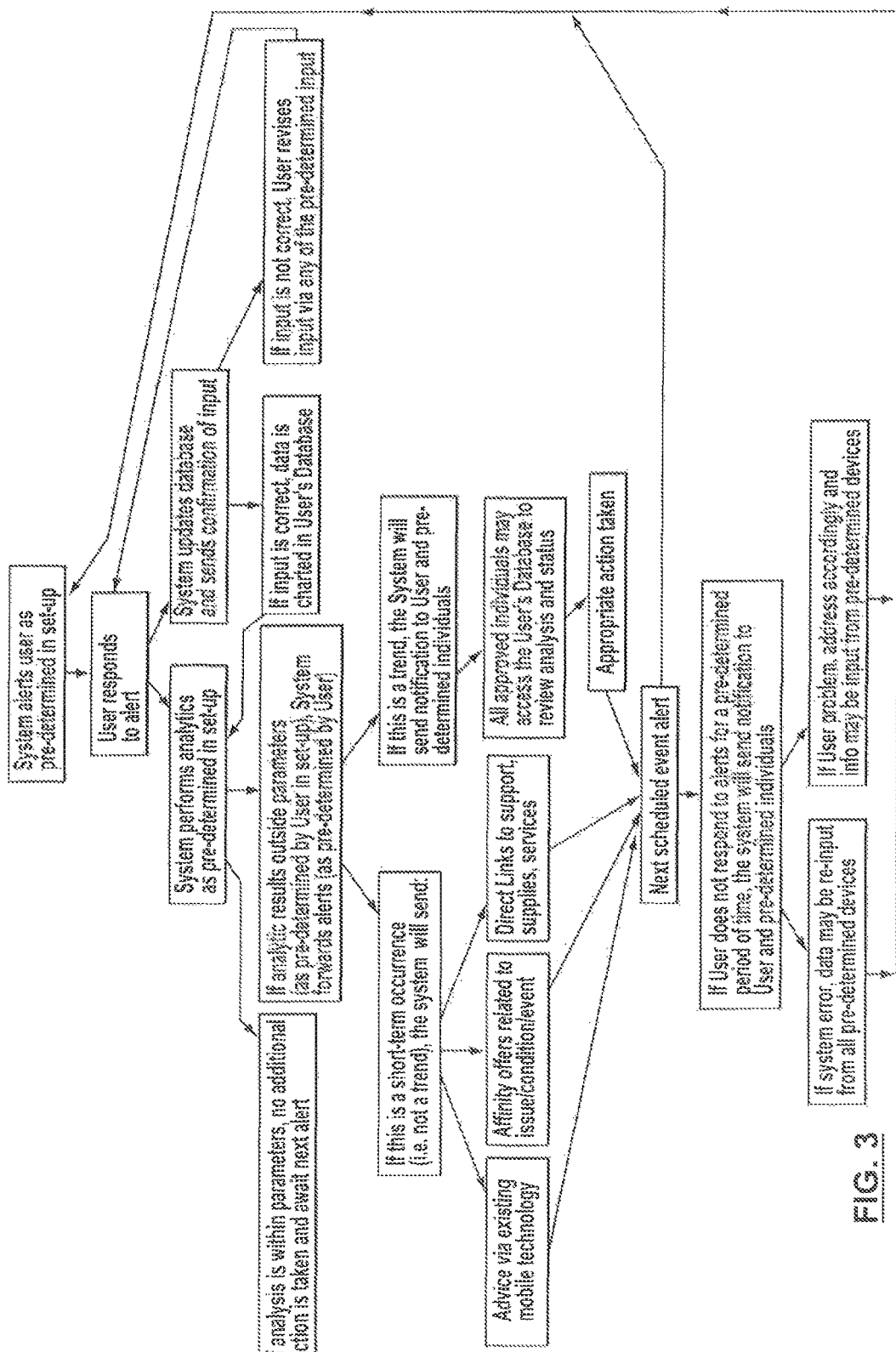
FIG. 3 is a flowchart illustrating a further aspect of the method illustrated in FIG. 2A, namely an active interface.

FIG. 3 illustrates a flow diagram of an exemplary process 300 for providing, by the user using input means, information to the system via the active interface. The active interface governs the relationship between the user and the system, including the responses provided by the user in response to a notification, and analysis that the system conducts.

Figure 4:
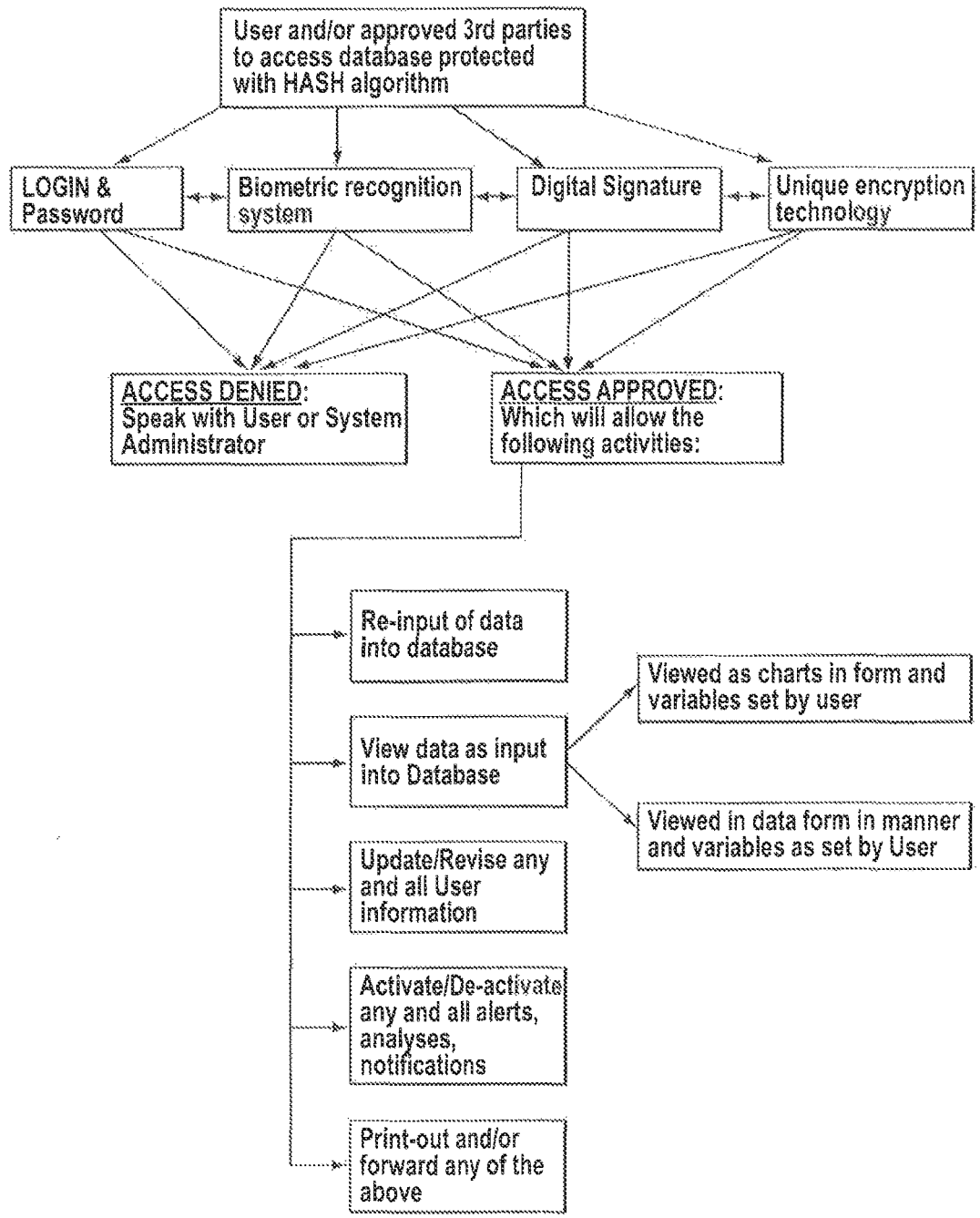
FIG. 4 is a flowchart illustrating a further aspect of the method illustrated in FIG. 2A, namely access to a database.

FIG. 4 illustrates a flow diagram of an exemplary process 400 for protecting the information provided by the user. As illustrated in FIG. 4, access to the database (18) is preferably protected by, for example, a HASH algorithm. This along with one or more other security techniques may ensure that the information remains secure.

Once the required parameters are specified, the user submits the info for approval through the Internet (14). The administrator receives the request for approval. If the request is not approved, the administrator deletes the request and user cannot go any further. If approved, the user is sent an e-mail for confirmation. When an e-mail sent, the user is also sent phone confirmation via SMS. Once the user replies, the system notifications are set.

In an embodiment, once the notification scheme is established, the system provides notifications to the user. The user responds to a notification, and the system assumes that any response prior to the next notification pertains to the preceding notification. The system performs trend analysis based on parameters selected by the user. The system determines whether response is within or outside such parameters. If it is within parameters, the system sends an SMS confirmation of the specific response. If outside the parameters, the system sends a confirmation of the specific response and provides additional notification that the user is outside its parameters. The system can also sends an e-mail notification to addresses as indicated and approved by the user in the application setup. These third parties (e.g., a family member or a caregiver) may access the user's database of information provided they have been given permission and the login and password information from the user.

In the event that the user does not respond for a specified period (with an example default setting being two days), the system will send an e-mail to the user notifying them of non-response and allowing them to review the account database to make required updates and/or to contact administrators/support.

In some embodiments, the user may access their database 18 via the website using their login/password and have the following options: (i) non-wireless input, namely the user has the option at any time to input information directly into database via a computer with Internet access: (ii) charted information, namely viewing of their raw data in date order (as chosen by user) or for specific date period (as chosen by user), or user may view their data on an animated bar chart in date order (as chosen by user) or for specific period (as chosen by user); (iii) the user can update or revise information, including the information at initial set-up, e.g., SMS number, password or e-mail address; (iv) the user may activate or deactivate any notifications at any time; and (v) the user may print-out the database information from the web interface.

Figure 5A:
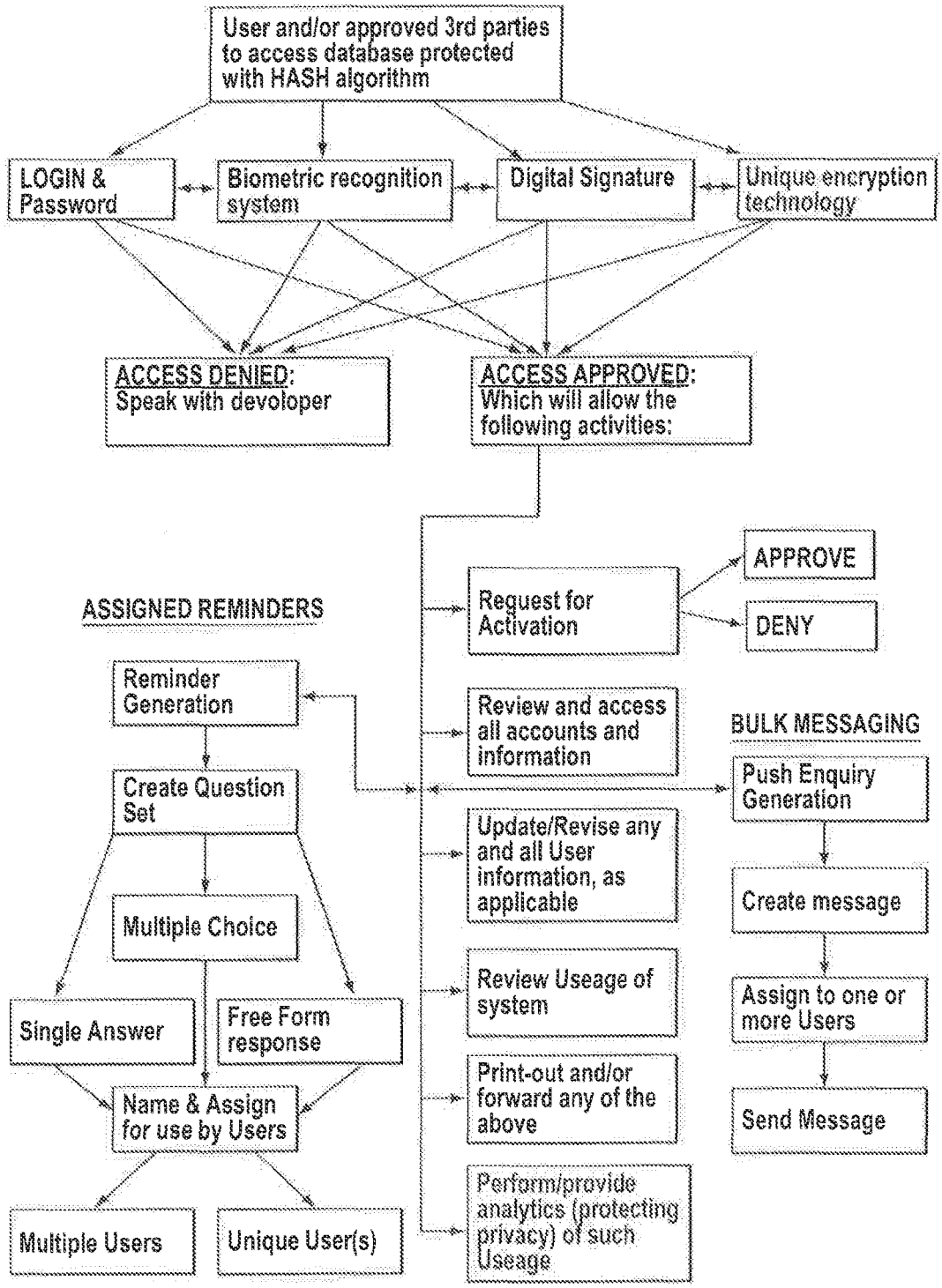
FIG. 5A is a flowchart illustrating a further aspect of the method illustrated in FIG. 2A, namely a system administrator interface.
Figure 5B:
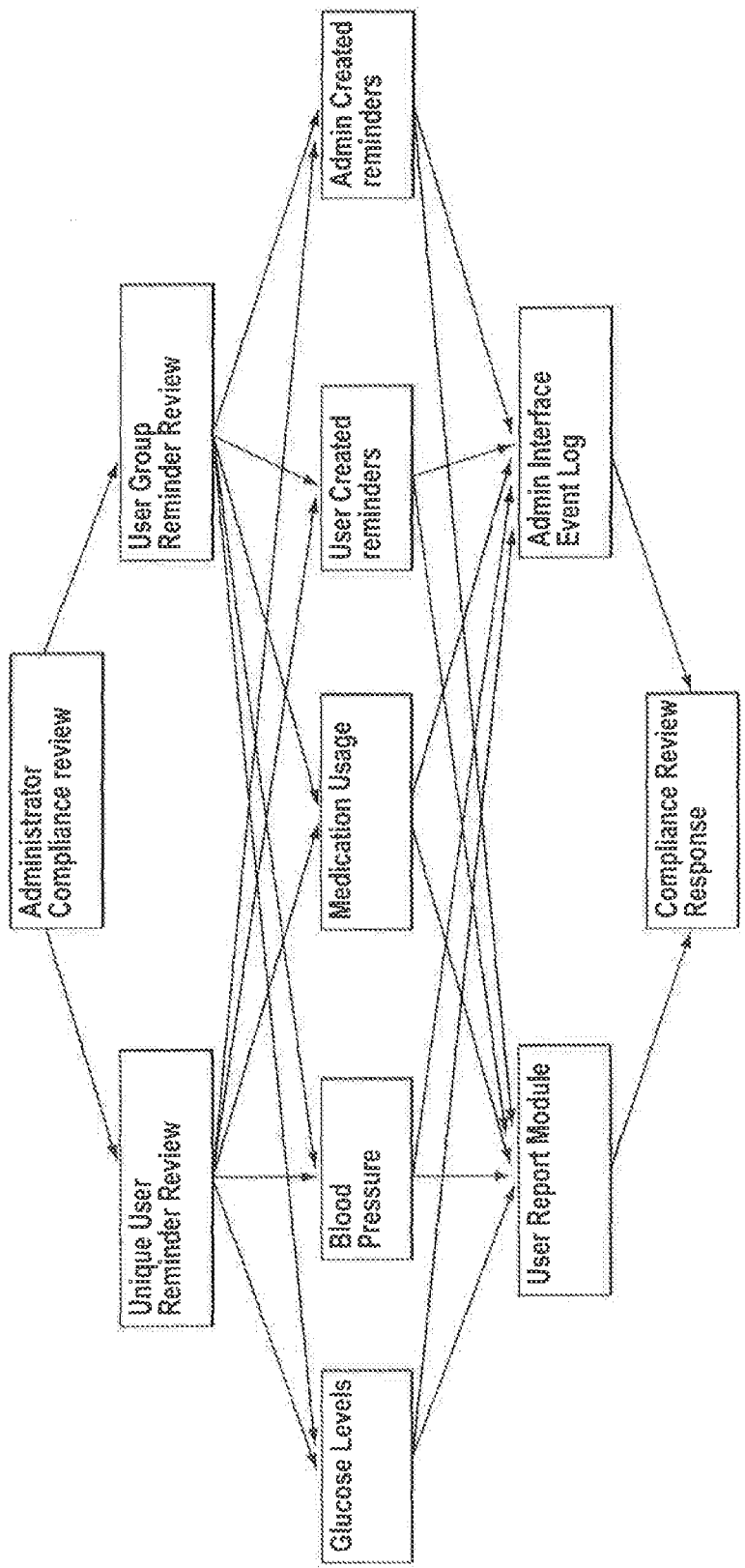
FIG. 5B is a flowchart illustrating a further aspect of the method illustrated in FIG. 2A, namely administrator user compliance review.

The administration interface of the disclosed system provides access to administrators to certain functions linked to the server 10. In an embodiment, these functions/resources are accessed via a series of web pages linked to the web server 12. The administration interface comprises a main page that prompts the user for login and password information. As an example, a flowchart illustrating a system administrator interface is provided in FIG. 5A. It should be understood that alternate means for authentication are also contemplated by the disclosed system. These web pages, for example, enable administrators to approve all requests for activation, review and access of all accounts (and respective databases), review usage of system via logs, etc., and provide an analysis of usage of system, accounts, etc. The administrator user compliance review is shown in FIG. 5B.

It should be understood that other functions/resources can be associated with the server (10) and made accessible via selection from possible options via user commands described in the present disclosure.

The disclosed system also provides for a plurality of notification types. In one embodiment, the notifications are provided by the server to the cellular phone in the form of enhanced text messaging. For example, the text notification can be a simple question, or multiple questions. In a further aspect, notifications can be multiple questions wherein each subsequent question is dependent on the previous response. The disclosed system also contemplates multiple notification options, including audio alerts, including musical alerts, voice alerts, and/or simple tones or ringing.

These audio notifications can be sent via MMS, and can be in mp3 or other suitable formats. A visual alert can be provided where such visual notifications are supported by the personal communication device (22). As mentioned herein, the notification can also be a direct alert linking to a third party, for example a family member or caregiver, as selected by the user. It should be understood that any notification or alert type mentioned herein can be implemented alone or in combination with other alert types, in accordance with the users' selection(s).

As mentioned, in yet a further aspect of the disclosed system musical notifications or alerts can be provided to the user through their personal communication device. In this regard, it is possible to correlate the particular musical piece to the various specific levels of notification or alert for the user. As an example, a notification comprising the song "Sugar, Sugar" can correspond to mild levels, whereas a notification comprising the song "No Sugar Tonight" can correspond to more serious levels. The parameter of these types of notifications can be set by the user and changed from time to time, in accordance with some embodiments.

In a further aspect of the disclosed system, the content of notifications can comprise specific information based on database analysis. For example, the notification content can be tailored (by the user) in relation to the database analysis relevant to, e.g., dietary requirements, exercise requirements, medical condition, individual reading or measurement, and/or support requirements.

In another aspect of the disclosed system, the data collected by the database (18) can be linked and provided to third party systems for further processing. For example, the data can be utilized for the purpose of patient record management or processing of insurance claims, subject to privacy issues.

In one specific example of the implementation of this aspect of the disclosed system, system 100 can be utilized by a pain management health provider. According to this implementation, data that is collected by system 100 concerning pain levels and medication use is provided to a patient record management system to improve the data available to the patient record management system.

The specific architecture to support this example implementation can be arranged as follows. A user can be fitted with a personal monitoring device that is operable to provide pain level and medication data (e.g., using BLUETOOTH™) to a personal communication device (e.g., a BLACKBERRY™). The personal communication device then provides this data to system 100, which acts as a communication broker with the pain management health provider. The pain management health provider provides for data normalization, data aggregation and secure storage, and is operable to interface with other services providers (e.g., emergency personnel, dentists, laboratory, pharmacy, etc.). Health records maintained by the pain management health provider can be directed to the particular user through their personal communication device, whether via system 100 or directly.

In yet further aspects of the disclosed system, notifications can comprise yet further information and content for the user. For example, a notification can take the form of a video of a caregiver, or even of the user themselves, giving a quick lecture about the current status, corresponding to the notification level. The notification can also provide links to sites, phone numbers, and suppliers relevant to the level. Alternatively, the notification can directly provide a tie-in, via text, cell, e-mail, web, camera, etc., to the particular caregiver or support individuals, as customized by the user. The present disclosure contemplates each one of these possible notifications/alerts, and any combination thereof, with the type of notification and any corresponding trend analysis customizable by the user.

The information requested by each notification is dependent on the individual needs of the user. For example, for users interested in monitoring Diabetes-related attributes, the notifications will prompt the user for specific values, including, e.g., glucose levels, blood pressure data, heart rate, weight, temperature, etc. The disclosed system is capable of interactively monitoring a plurality of measurements.

Tailoring the content of notifications may further improve the user's success at achieving adherence/compliance to a particular health regime. In this regard, the notifications can be changed on a regular basis, and can incorporate effects or entertainment elements to make them more interesting and engaging, for example through the use of comedy.

Further, the disclosed system is not limited to quantitative information but is also operable to prompt the user for specific non-quantitative health or lifestyle related information related to any of the applications discussed herein. For example, the notification can consist of a simple question, such as "How do you feel?", "Do you feel alert?", and "Do you feel tired?", etc. This in turn can result in additional questions to where these qualitative questions can further yield helpful information from the user and can be correlated to other data via the data analysis aspect of the disclosed embodiments. Such non-quantitative health or lifestyle related areas include dietary issues, mental health such as anxiety and exercise, to name a few.

EXAMPLE

In some embodiments, system 100 is used to record glucose measurements for Diabetics. The system server notifies the patient to take his or her glucose readings from their glucometer. The patient then inputs the information and the database responds with both a confirmation of the level and notification if the levels on average are rising or falling. In the event that the level remains high or low for a determined period of time, the patient-designated individuals (caregiver, parent, physician or other) is emailed a notification to that effect.

It is to be understood that monitoring of Diabetes-related conditions is only an example of the present disclosure, and the disclosed embodiments have a plurality of applications, as detailed in the foregoing.

Figure 6:
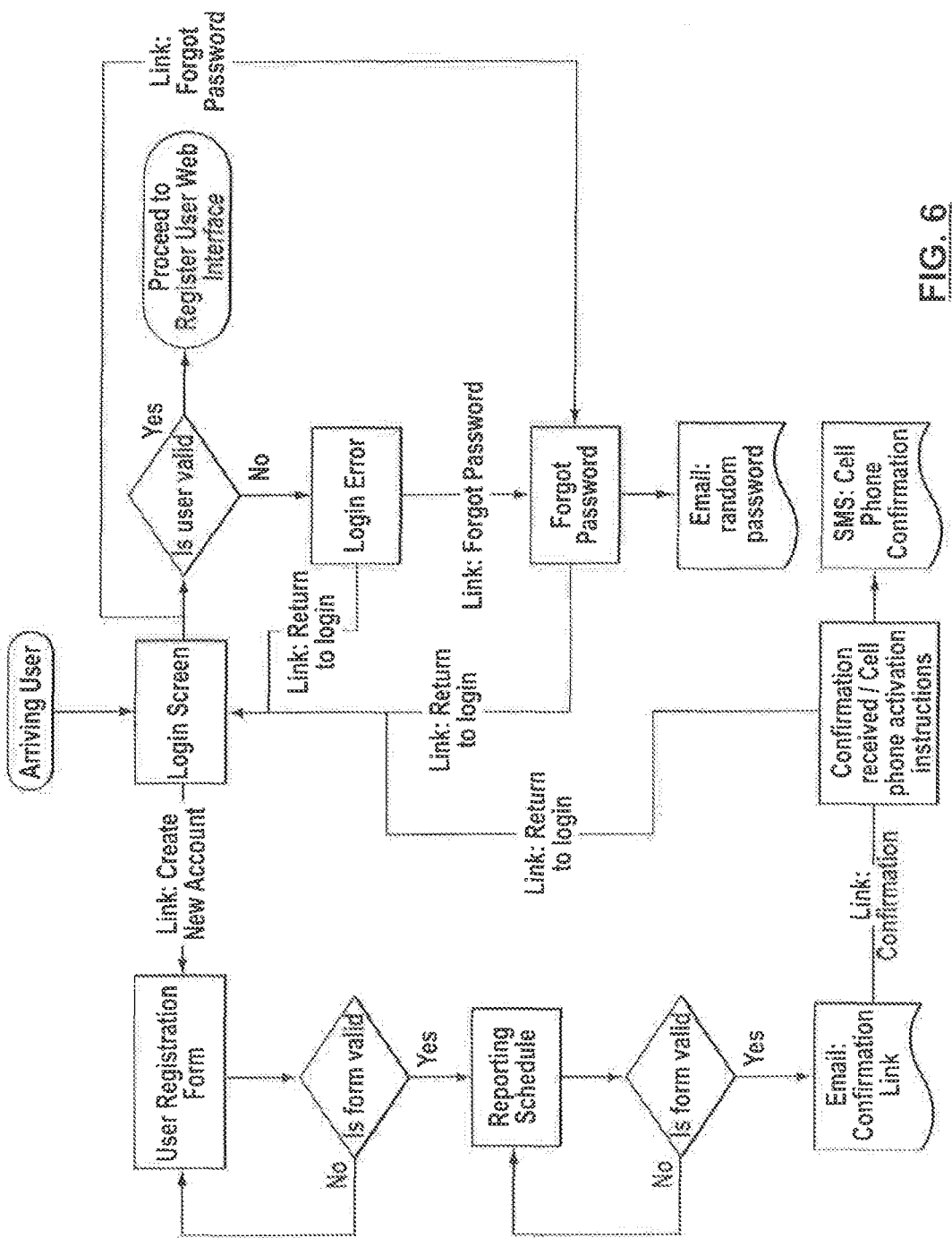
FIG. 6 is a flowchart illustrating a further aspect of one particular embodiment of the present disclosure, namely a user login and registration system.
Figure 7:
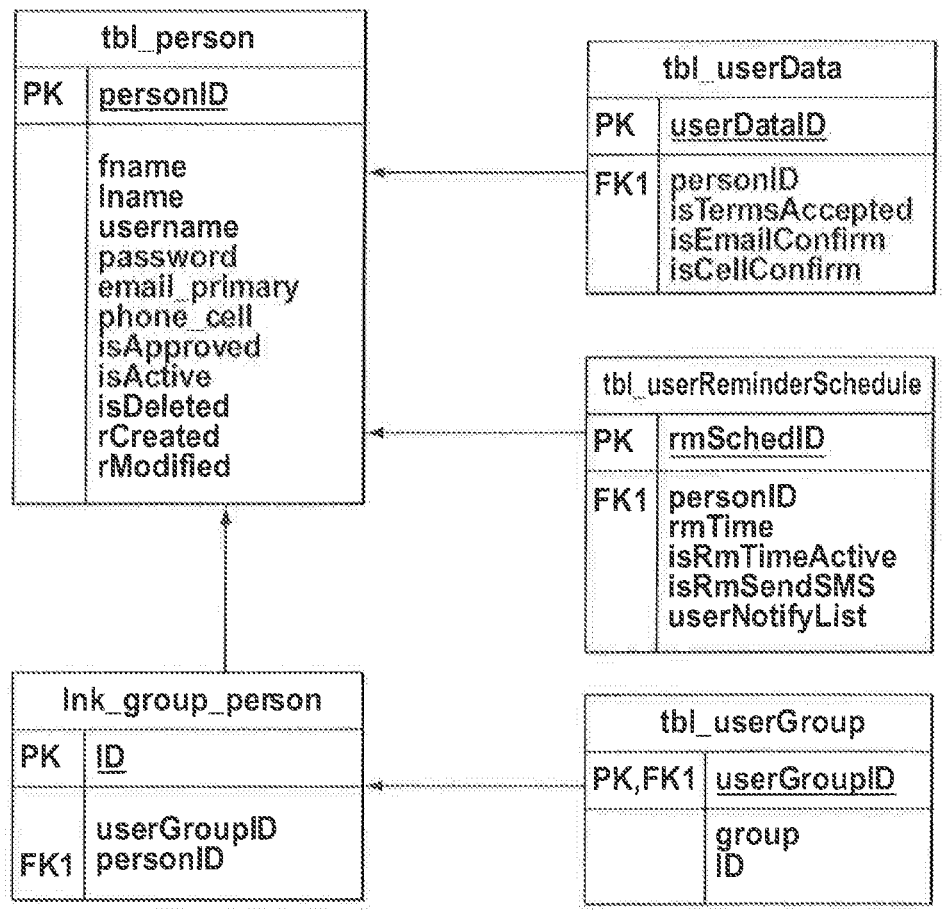
FIG. 7 is a flowchart illustrating a further aspect of one particular embodiment of the present disclosure, namely database schema requirements for the user login and registration system depicted in FIG. 6.
Figure 8:
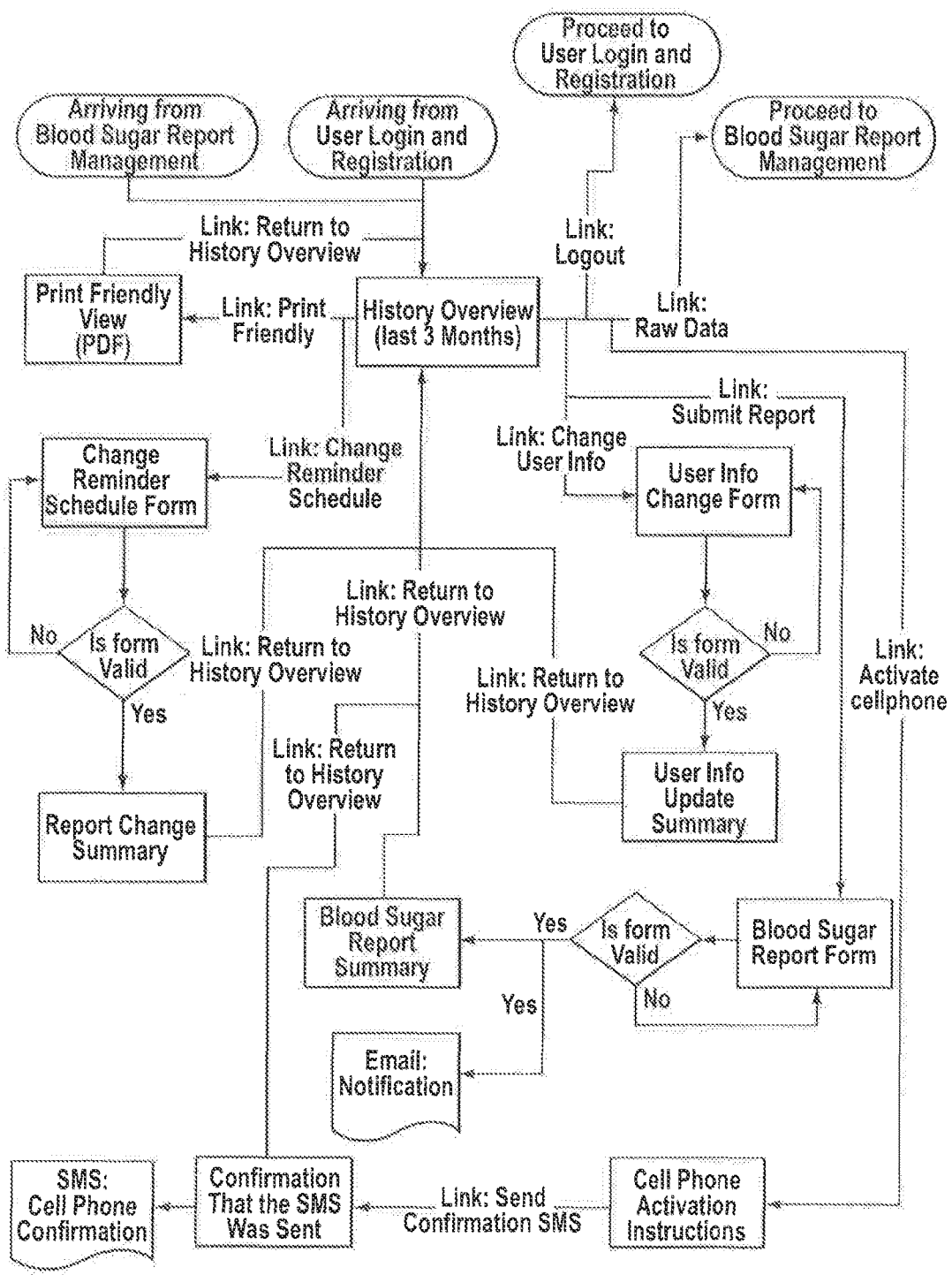
FIG. 8 is a flowchart illustrating a further aspect of one particular embodiment of the present disclosure, namely a registered user web interface.
Figures 10, 11, 12:
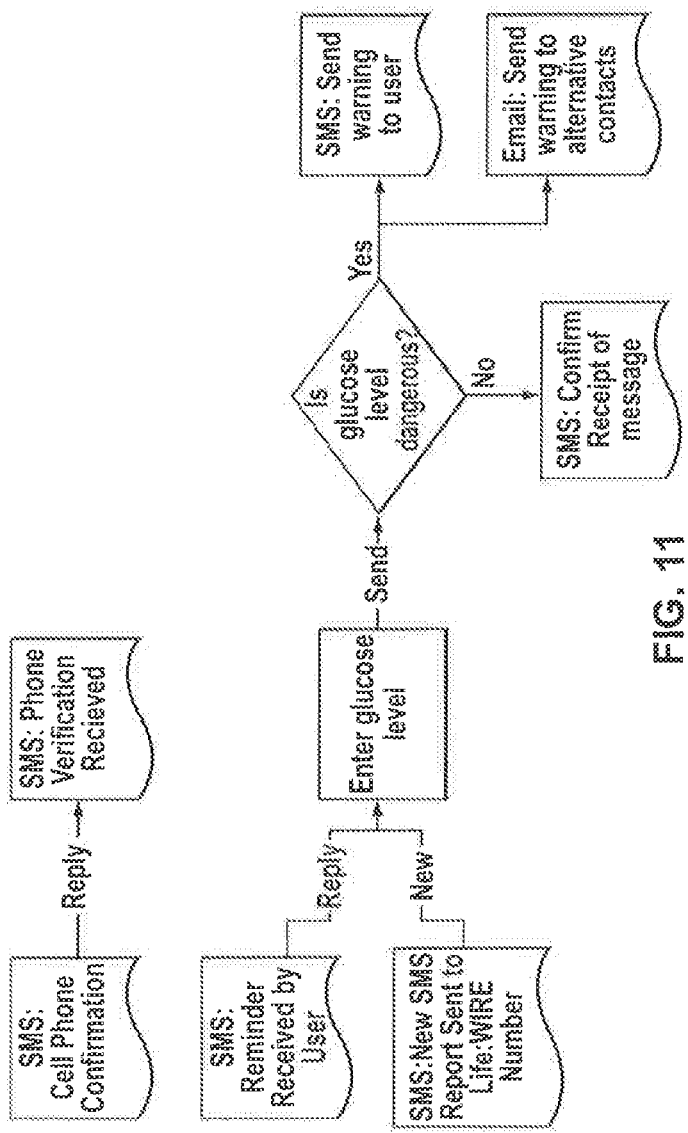
FIG. 10 is a flowchart illustrating a further aspect of one particular embodiment of the present disclosure, namely database schema requirements for the blood sugar report management system depicted in FIG. 9.
FIG. 11 is a flowchart illustrating a further aspect of one particular embodiment of the present disclosure, namely a mobile reporting system.
FIG. 12 is a flowchart illustrating a further aspect of one particular embodiment of the present disclosure, namely database schema requirements for the mobile reporting system depicted in FIG. 11.
Figures 13, 14:
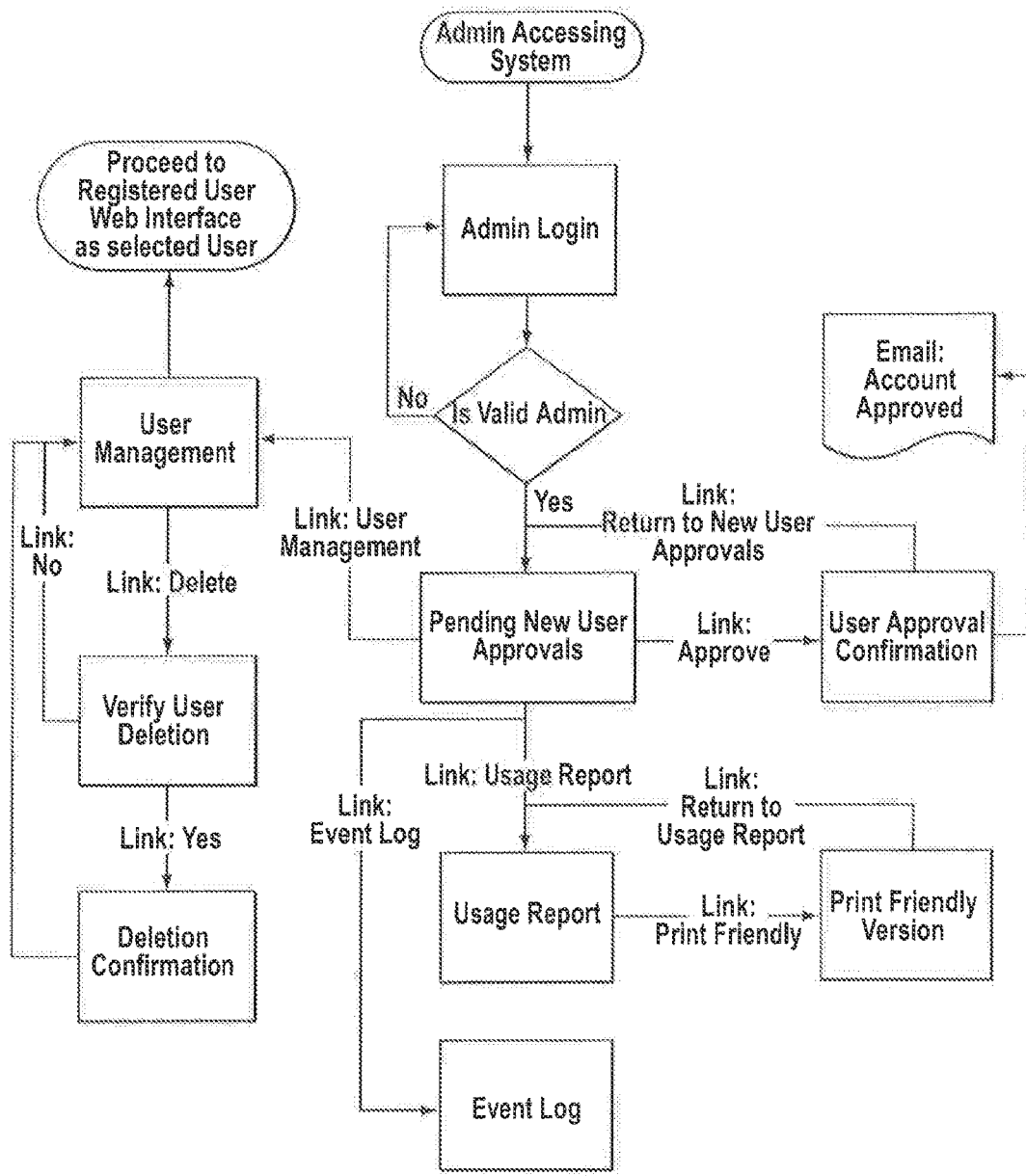
FIG. 13 is a flowchart illustrating a further aspect of one particular embodiment of the present disclosure, namely an administration interface.
FIG. 14 is a flowchart illustrating a further aspect of one particular embodiment of the present disclosure, namely database schema requirements for the administration interface depicted in FIG. 13.

More particular aspects of the example are described below and are further illustrated by reference to the Figs. Specifically: (A) FIG. 6 is a flowchart illustrating a further aspect of one particular embodiment of the present disclosure, namely a user login and registration system; (B) FIG. 7 is a flowchart illustrating a further aspect of some embodiments, namely database schema requirements for the user login and registration system depicted in FIG. 6; (C) FIG. 8 is a flowchart illustrating a further aspect of some embodiments, namely a registered user web interface; (D) FIG. 9 is a flowchart illustrating a further aspect of some embodiments, namely a blood sugar report management system; (E) FIG. 10 is a flowchart illustrating a further aspect of some embodiments, namely database schema requirements for the blood sugar report management system depicted in FIG. 9; (F) FIG. 11 is a flowchart illustrating a further aspect of some embodiments, namely a mobile reporting system; (G) FIG. 12 is a flowchart illustrating a further aspect of some embodiments, namely database schema requirements for the mobile reporting system depicted in FIG. 11; (H) FIG. 13 is a flowchart illustrating a further aspect of some embodiments, namely an administration interface; and (I) FIG. 14 is a flowchart illustrating a further aspect of some embodiments, namely database schema requirements for the administration interface depicted in FIG. 13.

1. User Login and Registration System

In some embodiments, every new and registered user accessing the system will require a username (which can be an e-mail address) and password. This system is illustrated in FIG. 6; the database schema requirements for this are illustrated in FIG. 7.

(a) Login Screen

In some embodiments, the login screen will be the default page seen by any user attempting to access the site that is not logged in. The page will allow the user to enter their username (e-mail address) and password and then click a login button to confirm that their credentials are valid. Should the user information provided prove valid, the user will proceed to the "History Overview" page which is covered under the "Registered User Web Interface". Should the credentials the user supplied be invalid, the user will be sent to the "Login Error" page that is detailed below.

This login screen will also include a link labelled "Forgot Password?". This link will lead to a webpage that will allow a user to receive a new password via e-mail.

There will also be a link labelled "Create New Account". When a new user arrives at the site they would use this like to begin the account creation process.

Users will be assigned to specific roles within the system. These roles include administrators, alpha testers, beta testers and general users. The user roles are set in the tbl_userGroup table and can be adjusted as needed. The roles control what functionality the users have access to within the system.

(b) Login Error

Should the user's credentials be invalid, they will be directed to this page. They will be notified that there has been a problem with the information they supplied and provided options to proceed.

The user will be able to use a link to return to the "Login Screen". There will also be a link to the "Forgot Password?" system.

Finally, there will be the option to "Create a new account" that will link the user to the "User Registration Form".

(c) User Registration Form

In some embodiments, the user registration form is the first step in creating a new account. The user must provide his/her first and last name, a valid e-mail address that will also act as their username, the cell number they wish use, and a password. The password field will be masked so users will be required to enter it twice to ensure that they do not make a mistake. Once the user has completed the registration form they will click the "Next" button to continue to the "Reminder Schedule" page. During the submission process, the data that the user entered will be verified and, should a field have been left blank or was filled-in incorrectly, the browser will return to the "User Registration Form" with the errors highlighted at the top of the page.

(d) Reporting Schedule

Once a user has completed the "User Registration Form", they will be asked to fill in the "Reporting Schedule". The user will be presented with the option to input as many notifications, which in this case are reminders, as they choose and at which time they would like to have the reminder sent. They will also have the option to determine the nature of the reminders such as requiring the input of glucose levels or confirmation of having taken medication. The user will be able to change these times, and nature of reminders and they will also have the ability to turn any or all of the reminders off. They will also have the option of setting a reporting time but not having that time send out an SMS reminder.

Under the reminder time area will be three blank text boxes where the user can enter in e-mail addresses. These three e-mail addresses will be copied on any notifications that are sent the user's cell phone. The e-mail fields can be left blank.

In addition, the user will set their personal settings which allows the user to create the parameters under which the system analyses the respective data trends. For example, in the measurement of glucose levels, it will allow for the user to determine the upper and lower limits and the number of measurements to use for such analysis. If the data trends go above or below such parameters, the system will send a notification of that event to the pre-determined above When the user has completed the form, they will click on the next button to continue. The page will check the times to make sure that they do not overlap.

Once the process has been completed, the page will display a thank you message and a note stating that a confirmation e-mail has been sent. The confirmation e-mail will contain a link that will have to be clicked on to verify the validity of the account. More information on the e-mail can be found below.

The scheduled reminders will be stored in the tbl_userRemindersSchedule table, as illustrated in FIG. 7. This table is designed to be scalable so that the number of reminders is scalable as the system is further developed. For this example, users will be limited to and prompted to use up to six reminders, however this is a soft requirement based on the forms and not the data structure.

(e) E-mail: Confirmation Link

Once the user has completed the various web forms that are required to create an account they will receive an e-mail. This e-mail contains a link that returns the user to the website and confirms that the e-mail account that is associated with the new account is in fact accessible to the user. The link will send the user to the "Confirmation Received/Cell Phone Activation Instructions".

(f) Confirmation Received/Cell Phone Activation Instructions

When a user clicks on the link supplied to them in the "E-mail: Confirmation Link", they will be sent to this page. The page will confirm that the user's web account will be activated once an administrator approves the account. The page will also inform the user that a SMS message has been sent to their cell phone. "SMS: Cell Phone Confirmation" section has more information on the details of the message. This page will also contain a link back to the "Login Screen" and the text for that link should read "Back to User Login".

(g) Forgot Password

Should a user have forgotten their password, they will be able to use the "Forgot Password" page to retrieve it. The user will be asked to enter the e-mail address they used to create their account and then hit a "Send Password" button. The page will then create a random password for the user's account and send that password to the user in an e-mail. More information on the e-mail can be found under the heading "E-mail: Random Password". Should the e-mail address entered not be registered with the system, the page will inform the user that the e-mail is not recognized.

(h) E-Mail: Random Password

Should the user forget their password, they can request that the site create a new one and e-mail it to them. They will then receive an email that contains a new randomly generated password.

2. Registered User Web Interface

In some embodiments, when a user wishes to review their blood sugar report history or make changes to their user account information, they will be able to do so via the "Registered User Web Interface". This interface is illustrated in FIG. 8. A user will need to have an account registered with the system and be logged in.

(a) Navigation System

A universal navigation system will be present on every page that is part of the web-based interface that a user interacts with while logged in. The navigation system will include links to the following locations: "History Overview"; "Blood Sugar Report Form"; "Blood Sugar Report Management"; "Change Reporting Schedule"; "Change User Information"; "Cell Phone Activation" (only appears if cell not active); and "Logout".

(b) History Overview

When the user logs into the web site, they have the option to come to this page. The page is meant to summarize the most recent data based on the user's reporting. The user will be presented with a bar chart of their average blood sugar level on a weekly basis. They will also see a graph of their reporting history displayed with each row containing a full day of reports.

The user will be able to adjust both the total time frame of the blood sugar chart displays (1 month, 2 months, 3 months, etc.) as well as the time each bar represents (daily, weekly etc.). Should a user's account not contain enough data to fill the requested time frame, the bars that do not have data will be set to zero.

The graph of reported data will adjust to the number of reporting times the user has set-up. For example, if the user has opted to only report their blood sugar 3 times per day, each day will only show 3 reports. The chart will display reports from newest to oldest. The user will also have the option to view a print-friendly version of this page that they can take with them to their 3-month check-up.

(c) Print-Friendly View (History Overview)

Should a user wish to print a version of the "History Overview", they will click on the "Print-Friendly" link on that page. They will be presented with a page containing only the historical data (both chart and graph) that is formatted to fit within the margins of a standard 8"×11" sheet. There will be a link on this page that will return the user to the "History Overview".

(d) Change Reporting Schedule Form

Through the use of the system a user may decide that their original reporting schedule is not working. They will be able to use the "Change Reporting Schedule Form" to make changes to these settings. The page will work very much like the "Reporting Schedule", barring a few exceptions. The first is that rather than a blank form appearing, the page will automatically fill in all fields with the current user's information. The second variation is that once the user has submitted the form they will be sent to the "Reporting Change Summary". The form will be verified against the same criteria as the "Reporting Schedule".

(e) Reporting Change Summary

Once the user has submitted the changes they would like to see to their reporting schedule they will be sent to this page. The page will contain a summary of their new information and verification that the changes have been made. A link at the end of the summary will lead the user back the "History Overview" page.

(f) User Info Change Form

If the user needs to make a change to their account information they will be able to do so via this form. This form is very much like the "User Registration Form" with a few exceptions, namely the form will be filled-in with the current user's account information when it loads, and the user will not be able to change their e-mail address. Once the user has completed the form and the data has been verified as properly entered the user will be sent to the "User Info Update Summary".

(g) User Info Update Summary

Once a user has updated their user information they will be sent to this page. The page will display their updated user information and confirm that the database has been changed. Should the user have changed the cell number that is associated with their account, the summary page will send out a "SMS: Cell Phone Continuation" message, as the new number will need to be confirmed before it is used. The page will also have a link back to the "History Overview" page.

(h) User Info Update Summary

Once a user has updated their user information they will be sent to this page. The page will display their updated user information and confirm that the database has been changed. Should the user have changed the cell number that is associated with their account the summary page will send out a "SMS: Cell Phone Confirmation" message, as the new number will need to be confirmed before it is used. The page will also have a link back to the "History Overview" page.

(i) Blood Sugar Report Summary

Once an online blood sugar report is successfully entered into the system, the user will be sent to this page where they will see a confirmation of their submission and be presented with a link back to the "Historical Overview". Should the user's average blood sugar be outside of the recommended range over the past 10 reports, the system will show a warning message on this page and send out an "Email: Notification" to requested recipients. This will occur unless the report entered is more than one day old.

(j) Cell Phone Activation Instructions

Should the user have ignored or deleted the original "SMS: Cell Phone Confirmation" that was sent to them during the account creation process, they will be able to use this system to confirm their cell phone number at any time. This page will give the user instructions on the confirmation process followed by a link to the "Confirmation that the SMS was sent" page.

(k) Confirmation that the SMS was Sent

The user will be notified that an SMS message has been sent to their cell number and that they should reply to it in order to confirm their cell number. The user will then follow a link at the bottom of the page back to the "History Overview" page. The rest of the process is covered under the "Mobile Reporting" section of this document.

3. Blood Sugar Report Management System

In some embodiments, a user may want or be required to change or delete blood sugar reports. This may be due to errors made during the reporting process. The "Blood Sugar Report Management System" is an interface that will allow user to manage their blood sugar reports. This system is illustrated in FIG. 9; the database schema requirements are illustrated in FIG. 10.

(a) Report List

This page will show a list of reports. The reports will be in the form of a table and the user will have several options to alter the view. Each record will have links associated with them that will allow the user to either edit or delete the record.

Due to the potential number of records that could be displayed, the page will only show 20 records at a time. The user will be allowed to scroll through the reports 20 records at a time.

The user will also be able to refine the number of records shown by restricting the time frame. The user will be able to set a start date and end date and any records that where entered during the specified period will be displayed.

The reports will be displayed in a chart. "Edit" and "Delete" found in the command column will be links to the "Edit Form" and "Deletion Confirmation" pages, respectively. They will allow the user to perform either operation on the specific report with which they are associated. The page will also have a link to the "Print-Friendly View (Report List)" page.

(b) Print-Friendly View (Report List)

Should a user wish to print out a version of the "Report List", they will click on the "Print-Friendly" link on that page. They will be presented with a page only containing all the reports in the selected time frame formatted to fit within the margins of a standard 8"×11" sheet. There will be a link on this page that will return the user to the "Report List" page.

(c) Edit Form

The user can select to edit a blood sugar report from the "Report List", which will lead them to this page. The user will be able to change the date, time, and blood sugar level associated with the record. Once the user has made the necessary adjustments they can submit their changes, at which point any error will be reported. If the record is acceptable the user will be sent to the "Edit Summary" page. Any alteration will not trigger a warning to be sent out.

(d) Edit Summary

Once a blood sugar record has been updated the user will be shown a summary of the changes they have made on this page. The user will then be presented with a link back to the "Report List" page.

(e) Deletion Confirmation

Should a user select to delete a record from the "Record List", they will be sent to this page. They will be asked to confirm the deletion request. If they click on 'Yes' the user will be sent to the "Deletion Confirmed" page. If they select 'No' the user will return to the "Report List" page.

(f) Deletion Confirmed

The user will be sent to this page once they have confirmed that they would like to delete a specific record. The page will confirm that the record has in fact been removed from the database. The user will then be able to take a link back to the "Report List".

4. Mobile Reporting

According to an embodiment, most of the day-to-day interaction with the system will be conducted via the cell phone rather than on the web.

One aspect of this mobile reporting is the reporting window. Should a user register six reporting times in one day, they have created six windows during which time they must submit their reports. For example, a user has set their first reporting time to start at 9 am and the next to start at 12 pm. Any message sent in between these two times will be considered a valid first window report and will show up on their report chart under the heading 1. Should the system receive two reports during one of these windows, only the first report will be considered valid.

An issue facing the mobile portion of the system is what to do when a user leaves a cell area or turns off their cell for long periods of time. The SMS system will be required to identify that a user is not receiving messages and stop sending in order to avoid messages piling up and reduce any sending cost that may be incurred. The server will need to be able to recognize when the user has reconnected and resume sending messages at that point.

The mobile reporting system is illustrated in FIG. 11; the database schema requirements are illustrated in FIG. 12.

(a) SMS: Cell Phone Confirmation

At various times a user will need to confirm that they have access to the cell phone number they have provided. The confirmation process will start with this message being received by the user's cell phone. The message will instruct the user to simply reply to the message with the letter "Y" to confirm that they wish their cell phone to receive messages from the system.

(b) SMS: Phone Verification Received

Once a user replies to the "SMS: Cell Phone Confirmation" and the server has successfully received their confirmation message, the user will be sent a follow-up message informing the user that their phone will now receive reminders.

(c) SMS: Reminder Received by User

The server will send out a reminder to the user's cell phone at specified times requested by the user. This message will inform the user that they should check their glucose levels and reply to the message with the result. The user should then reply to the message to report their blood sugar level. Any report the user sends back prior to the next reporting window commencing will be considered a successful response to this message.

(d) SMS: New SMS Report Sent to the System

In some instances, a user may request not to be sent a reminder yet still wish to report their blood sugar. They would be able to do so by sending a message to a number associated with the system, to report their glucose level.

(e) Enter Glucose Level

The user will be required to enter in their blood sugar level as reported by their glucometer into a text message and send it to the SMS number. This process will require the user to be able to enter in numbers and decimal places via their cell phone.

When a user enters their blood sugar, the system will assume that they are entering in a number with at least one decimal place. Should the user enter a decimal point into their blood sugar level they submit, the system will accept the message as it is sent. Should the user not put in a decimal point, the system will assume that the last digit is after the decimal place. For example, 112 would be converted to 11.2.

(f) SMS: Confirm Receipt of Report

The server will send the user a confirmation that their blood sugar report was received and display how their report was interpreted by the system. This message will only be sent out if the user's blood sugar level does not trigger a warning.

(g) SMS: Send Warning to User

If a user's average blood sugar is outside of recommended bounds over the last 10 reports, the user will be sent a warning message that displays their current average blood sugar level and inform them that it is too high or low and that the user should take action in order to correct the variance. In addition, should a user's blood sugar have been well maintained during this period, a message will be sent stating that they have stayed within their desired range on average over the last ten reports.

(h) E-Mail: Send Warning to Alternative Contacts

Should a user's report indicate that their average blood sugar level over the last 10 reports is out of the recommended range, all the alternative e-mail addresses registered to their account will receive and e-mail copy of the warning.

5. Administration Interface

In some embodiments, administrators may require an interface that will allow them to perform administrative tasks on the system and view usage statistics. This portion of the system will not be accessible to the public and will require an administrator (admin) to login with a special username and password.

The administration interface is illustrated in FIG. 13; the database schema requirements are illustrated in FIG. 14.

(a) Admin Login

An administrator (or "admin") wishing to access the administration interface will go to a special web address that will bring them to the administrator login screen; at which point they will be required to enter in a username and password. Should the administrator enter in a valid username and password they will proceed to the "Pending New User Approvals" page. Should the login criteria the user supplied prove invalid, they will return to the login screen which will display an error message.

(b) Admin Navigation System

An admin navigation system will be present on every page that is part of the admin interface and that is accessible while logged in. The navigation system will include links to the following locations: "Pending New User Approvals"; "User Management"; "Usage Report"; "Event Log"; and "Logout".

(c) Pending New User Approvals

Once an administrator has successfully logged in, they will be presented with a list of new user accounts that are awaiting approval. The list will only show accounts that have never been approved before.

User information is listed in a chart. The first field will show the user's name, the second will show their email address. A field marked "E-mail Conf" will show weather the user has confirmed their e-mail address with the system. Similarly, the "Cell Conf" field shows whether the user has successfully registered their cell with the system. The last column contains a link called "Approve" should an admin click on the approve button the users account will be activated and the admin will be sent to the "User Approval Confirmation" page. The admin will also have the option to delete the new account which will send the admin to the "Verify User Deletion" page.

(d) User Approval Confirmation

Once an admin has approved a new user, the admin will arrive at this page where they will see a notice that the user has been successfully approved and that the "E-mail: Account Approved" has been sent to the user notifying them of the activation of their account. The page will include a link back to the "Pending New User Approvals" page.

(e) E-Mail: Account Approved

Once an admin has approved a user's account, the system sends the user a copy of this e-mail. They will be notified that they may now log into the system.

(f) User Management

Throughout the course of the normal operation of the system, admins may be required to aid users with system problems or perhaps delete accounts that are no longer in use. The "User Management" page will allow the admin to view all the current approved accounts in the system. The chart therein is very similar to the one described under the "Pending New User Approvals" section, however, it has one key difference. Under the command column, there is a link labelled "Login". Should the admin wish to investigate issues with a particular user's account, they can click this link to login as that user. This function is important as it allows an admin to help a user without the user having to reveal their password to the admin.

As the list of users may grow quite long, each page will only show 20 records at a time and the admin will be able to page through them 20 records at a time. They will also have the option of entering in part or a user's entire name to search for a specific account. Any accounts that match the criteria will be displayed so that partial names can be entered.

(g) Verify User Deletion

Should an admin decide that it is necessary to delete an account from the system, they will arrive at this page where they will be asked to confirm the decision. They will be presented with two links, the first will be labelled "Yes" which will send them to the "Deletion Confirmation" page. The link will return them back to the "User Management" page or the "Pending New User Approvals" page depending on where they initially clicked the delete link.

(h) Deletion Confirmation

Once an admin has confirmed that they do, in fact, wish to delete an account, they will see this page that will confirm that the user account has been deleted and provided them with a link back the either the "User Management" page or the "Pending New User Approvals" page depending on the status of the record that was deleted. A deleted account will not actually be purged from the database but rather flagged as deleted and ignored by the system. This is important for potential data recovery.

(i) Usage Report

As the main goal of this system is to prove its own validity, the usage statistics will be a very important part of the admin interface. The usage report will display the following statistics: "Total Number of Approved Accounts"; "Total Number of Approved Accounts with Activated Cell Phones"; "Total Number of SMS Messages Sent"; "Total Number of SMS Messages Received"; "Average Number of Reminders Responded To"; "Average Number of Reminders Ignored"; "Average Number of Report Windows Filled"; "Average Number of Report Windows Empty"; "Average Blood Sugar Level 3 Months Ago"; "Average Blood Sugar Level 2 Months Ago"; "Average Blood Sugar Level 1 Month Ago"; "Total Number of Users that Report 80-100% As Expected"; "Total Number of Users that Report 60-80% As Expected"; "Total Number of Users that Report 40-60% As Expected"; "Total Number of Users that Report 0-40% As Expected"; "Average Blood Sugar Level of Users with 80-100% Reporting"; "Average Blood Sugar Level of Users with 60-80% Reporting"; "Average Blood Sugar Level of Users with 40-60% Reporting"; and "Average Blood Sugar Level of Users with 0-40% Reporting".

An admin will also be able to produce a print-friendly version of the usage reports by clicking on the "Print-Friendly" Link.

(j) Print-Friendly Version (Usage Report)

Should a user wish to print a version of the "Usage Report" they will click on the "Print-Friendly" link on that page. They will be presented with a page containing only the usage statistics that are formatted to fit within the margins of a standard 8"×11" sheet. There will be a link on this page that will return the user to the Usage Report.

(k) Event Log

The event log is a simple chart of all the events that have occurred through the invention. The chart will have to fields: "Event Type" and "Message". There are four types of events that can occur: "User", "Admin", "System", and "Error". An admin will be able to view these logs 50 events at a time and will have the option to scroll through them. They will also be able to select a time frame to reduce the total number of records shown. The exact messages that will accompany each event will be determined during the production of the system. It is through the "Event Log" that administrators can monitor compliance of any element of the system. The "Event Log" displays all activities such as time that a reminder was triggered, to which user it relates (which has a unique identifier), when a reminder was sent (which has a unique identifier relating to each unique user), when a response was received and what response was provided by the user.

What is claimed is:

1. A computerized method of monitoring patient health using a patient-managed monitoring scheme, the method being performed by a server configured to manage a patient account associated with a patient and an administrator account associated with an administrator of the patient, the method comprising:
receiving, from the patient via a device associated with the patient account, a proposed monitoring scheme for the patient, the proposed monitoring scheme comprising monitoring scheme settings configured by the patient, the monitoring scheme settings including:
a query schedule for scheduling the transmission of a query to the device associated with the patient account, the query requesting response data; and
an alert criterion and an alert procedure for at least one attribute associated with the query or the response data;
activating the proposed monitoring scheme based on an approval information received from a device associated with the administrator account;
generating the query based on the query schedule of the activated monitoring scheme;
sending the generated query to the patient, via the device associated with the patient account, based on the query schedule; and
receiving the response data corresponding to the query from the device associated with the patient account.

2. The method of claim 1, wherein the patient account comprises a user tag associated with an item in the query, and the query is generated based in part on the user tag.

3. The method of claim 2, wherein the user tag includes at least one of a personalized message and a name of the patient, and the generating the query includes incorporating the at least one of the personalized message and the name of the patient in the query.

4. The method of claim 1, wherein the approval information includes modified settings for monitoring scheme settings and wherein the activating the proposed monitoring scheme includes incorporating the modified settings into the proposed monitoring scheme.

5. The method of claim 4, wherein the modified settings for monitoring scheme settings include an additional query schedule, and the sending of the generated query is further based on the additional query schedule.

6. The method of claim 5, wherein the patient account comprises a user tag including a date and wherein the additional query schedule of the modified settings, is generated based on the date of the user tag.

7. The method of claim 2, wherein the user tag includes a contact information of a third party and wherein the method further comprises:
analyzing the response data; and
based on the analysis of the response data and the alert criterion, performing the alert procedure, wherein the alert procedure includes notifying the third party based on the contact information of the third party of the user tag.

8. The method of claim 1, wherein the method further comprises:
analyzing the response data; and
based on the analysis of the response data and the alert criterion, performing the alert procedure, wherein performing the alert procedure includes:
notifying the device associated with the administrator account;
causing the device associated with the administrator account to provide options to the user of the device associated with the administrator account, wherein the options include an option to send a set of additional queries to the device associated with the patient account.

9. The method of claim 8, wherein the set of additional queries is a validated query set.

10. The method of claim 1, further comprising:
analyzing the response data; and
based on the analysis of the response data and the alert criterion, loading and sending a set of preconfigured queries to the device associated with the patient.

11. The method of claim 10, wherein the loading of a set of preconfigured queries to the device associated with the patient includes incorporating a value of a user tag into one or more queries of the set of preconfigured queries.

12. The method of claim 1, wherein the value of the user tag is a name of the patient.

13. The method of claim 1, further comprising:
analyzing the response data;
based on the analysis of the response data and the alert criterion, performing the alert procedure; and
loading a set of preconfigured queries corresponding to a result of the analysis of the response data and sending the set of preconfigured queries to the device associated with the patient.

14. The method of claim 1, further comprising:
receiving, from the device associated with the administrator account, a set of monitoring scheme settings; and
sending the set of monitoring scheme settings to the device associated with the patient account, wherein the received proposed monitoring scheme is configured by the patient via the device associated with the patient account based on the set of monitoring scheme settings.

15. The method of claim 1, further comprising sending to the device associated with the patient account at least one query based on an input data received from the device associated with the patient account.

16. A computerized system for monitoring patient health using a patient-managed monitoring scheme, the system being configured to manage a patient account associated with a patient and an administrator account associated with an administrator of the patient, the system comprising:
a memory storing instructions; and
at least one processor configured to execute the stored instructions to perform operations including:
receiving, from the patient via a device associated with the patient account, a proposed monitoring scheme for the patient, the proposed monitoring scheme comprising monitoring scheme settings configured by the patient, the monitoring scheme settings including:
- a query schedule for scheduling the transmission of a query to the device associated with the patient account, the query requesting response data; and
- an alert criterion and an alert procedure for at least one attribute associated with the query or the response data;

activating the proposed monitoring scheme based on an approval information received from a device associated with the administrator account;

generating the query based on the query schedule of the activated monitoring scheme;

sending the generated query to the patient, via the device associated with the patient account, based on the query schedule;

receiving the response data corresponding to the query from the device associated with the patient account;

analyzing the response data; and based on the analysis of the response data and the alert criterion, performing the alert procedure.

17. The system of claim 16, the operations further comprising causing a clinical interface to be displayed at the device associated with the administrator account, the clinical interface comprising a table view displaying a collection of response data from the device associated with the patient account.

18. The system of claim 17, wherein the table view includes a value representing a change in the response data over a period of time.

19. The system of claim 17, wherein the table view includes a value representing a cumulative mean of the response data.

20. The system of claim 17, wherein the table view includes a value calculated based on the response data received from devices associated with a plurality of patient accounts.

21. The system of claim 17, the operations further comprising causing the clinical interface to be updated at the device associated with the administrator account when an additional response data is received.

22. A computerized method of monitoring a user using a monitoring scheme, the method being performed by a server configured to manage a user account associated with the user and an administrator account associated with an administrator of the user, the method comprising:

receiving, from the user via a device associated with the user account, a proposed monitoring scheme for the user, the proposed monitoring scheme comprising monitoring scheme settings configured by the user, the monitoring scheme settings including:
- a query schedule for scheduling the transmission of a query to the device associated with the user account, the query requesting response data; and
- an alert criterion and an alert procedure for at least one attribute associated with the query or the response data;

activating the proposed monitoring scheme based on an approval information received from a device associated with the administrator account;

generating the query based on the query schedule of the activated monitoring scheme;

sending the generated query to the user, via the device associated with the user account, based on the query schedule; and receiving the response data corresponding to the query from the device associated with the user account.

* * * * *